US006294332B1

(12) United States Patent
Chabot

(10) Patent No.: US 6,294,332 B1
(45) Date of Patent: Sep. 25, 2001

(54) COMPOSITION AND METHODS FOR MODULATING THE LENGTH OF TELOMERES

(75) Inventor: Benoit Chabot, Sherbrooke (CA)

(73) Assignee: Telogene Inc., Fleurimont (CA)

( * ) Notice: Subject to any disclaimer, the term of this patent is extended or adjusted under 35 U.S.C. 154(b) by 0 days.

(21) Appl. No.: 09/214,178
(22) PCT Filed: Jun. 30, 1997
(86) PCT No.: PCT/CA97/00471
§ 371 Date: Feb. 25, 1999
§ 102(e) Date: Feb. 25, 1999
(87) PCT Pub. No.: WO98/00537
PCT Pub. Date: Jan. 8, 1998

Related U.S. Application Data
(60) Provisional application No. 60/020,956, filed on Jul. 1, 1996.

(51) Int. Cl.$^7$ .............................. C12Q 1/68; G01N 33/53; G01N 33/566; C12P 19/34; C12N 15/00; C12N 9/50; C07K 21/02
(52) U.S. Cl. .............................. 435/6; 435/7.1; 435/91.1; 435/91.5; 435/320.1; 435/219; 436/548; 436/501; 530/350; 536/23.1; 536/24.3; 536/24.31; 536/24.32; 536/24.33
(58) Field of Search .............................. 435/6, 91.1, 91.5, 435/320.1, 7.1, 219; 536/24.32, 24.31, 24.3, 24.33, 23.1; 935/77; 530/350

(56) References Cited

U.S. PATENT DOCUMENTS 5,489,508 * 2/1996 West et al. .............................. 435/6
5,837,857 * 11/1998 Villeponteau et al. ............. 536/24.1
5,994,062 * 11/1999 Mulshine et al. ........................ 435/6

FOREIGN PATENT DOCUMENTS

WO 93/23572   11/1993   (WO).
WO 95/13383    5/1995   (WO).
WO 96/41016   12/1996   (WO).
WO 97/08314    3/1997   (WO).
WO 97/11198    3/1997   (WO).
WO 98/11204    3/1998   (WO).
WO 98/11207   10/1998   (WO).

OTHER PUBLICATIONS

Rosenberg et al. Gene Therapist, Heal Thyself. vol. 287, No. 5459, p. 1751, Mar. 2000.*
Pandolfo et al., Single stranded DNA binding proteins derived from hnRNP proteins by proteolysis in mammalian cells. vol. 13, No. 18, pp. 6576–6590. Sep. 1985.*
Pandolfo et al., Single stranded DNA binding proteins derive from hnRNP proteins by proteolysis in mammalian cells, 1985, Nucleic Acids Research, 13: 6576–6590.
Riva et al., Mammalian single–stranded DNA binding protein UP I is derived from the hnRNP core protein A1, 1986, The Embo Journal, England, 5: 2267–2273.
Buvoli et al., Recombinant hnRNP protein A1 and its N–terminal domain show preferential affinity for oligodeoxynucleotides homologous to intron/exon acceptor sites, 1990, Nucleic Acids Research, 18: 6595–6600.
Conrad et al., Rap1 Protein Interacts with Yeast Telomeres In Vivo: Overproduction Alters Telomere Structure and Decreases Chromosomes Stability, 1990, Cell, 63: 739–750.
Ben–David et al., Retroviral Insertions Downstream of the Heterogeneous Nuclear Ribonucleoprotein A1 Gene in Erythroleukemia Cells: Evidence that A1 Is Not Essential for Cell Growth, 1992, Molecular and Cellular Biology, 12: 4449–4455.
McKay et al., hnRNP A2/B1 binds specifically to single stranded vertebrate telomeric repeat TTAGGGn, 1992, Nucleic Acids Research, 20, 6461–6464.
Dreyfuss et al., hnRNP Proteins and the Biogenesis of mRNA, 1993, Annu. Rev. Biochem, 62:289–321.
Ishikawa et al., Nuclear Proteins That Bind the Pre–mRNA 3' Splice Site Sequence r(UUAG/G) and the Human Telomeric DNA Sequence d(TTAGGG)n, 1993, Molecular and Cellular Biology, USA, 4301–4310.
Burd et al., RNA binding specificity of hnRNP A1: significance of hnRNP A1 high–affinity binding sites in pre–mRNA splicing, 1994, The Embo Journal, England, 13: 1197–1204.
De Lange, Titia, Activation of telomerase in a human tumor, 1994, Proc. Natl. Acad, Sci,. USA, 91: 2882–2885.
Kim et al., Specific Association of Human Telomerase Activity with Immortal Cells and Cancer, 1994, Science, 266: 2011–2015.
Mayeda et al., Function of conserved domains of hnRNP A1 and other hnRNP A/B proteins, 1994, The Embo Journal, England, 13, 5483–5495.
Yang et al., The A1 and A1B proteins of heterogenous nuclear ribonucleoparticles modulate 5' splice site selection in vivo, 1994, Proc. Natl. Sci, USA, 91: 6924–6928.
Bryan et al., Telomere elongation in immortal human cells without detectable telomerse activity, 1995, The EMBO Journal, England, 14, 4240–4248.

(List continued on next page.)

Primary Examiner—Stephanie Zitomer
Assistant Examiner—Cynthia B. Wilder
(74) Attorney, Agent, or Firm—Clark & Elbing LLP; Kristina Bieker-Brady

(57) ABSTRACT

The present invention relates to the length of telomeres and the role of hnRNP A1, UP1 or derivatives thereon. More particularly, the present invention relates to hnRNP A1, UP1 or derivatives thereof to maintain or alter the length of telomeres in cells. The present invention also relates to methods and compositions for increasing or decreasing the proliferative capacity of cells and to delay or precipitate the onset of senescence The invention further relates to hnRNP A1 or UP1 or derivatives thereof as pharmaceutical, therapeutic and diagnostic reagents.

21 Claims, 5 Drawing Sheets

OTHER PUBLICATIONS

De Lange Titia, Telomere Dynamic and Genome Instability in Human Cancer, 1995, Telomeres, Cold Spring Harbor Laboratory Press: 265–293.

Feng et al., The RNA Component of Human Telomerase, 1995, Science 269: 1236–1241.

Rogan et al., Alterations in p53 and p161NK4 Expression and Telomere Length during Spontaneous Immortalization of Li–Fraumeni Syndrome Fibroblasts, 1995, Molecular and Cellular Biology, USA, 15: 4745–4753.

Zakian, Virginia A., Telomeres: Begining to Understand the End, 1995, Science, 270: 1601–1607.

Broccoli et al., Telomerase Activation in Mouse Mammary Tumors: Lack of Detectable Telomere Shortening and Evidence for Regulation of Telomerase RNA with Cell Proliferation, 1996, Molecular and Cellular Biology, 16: 3765–3772.*

De Lange, Titia, In search of vertebrate telomeric proteins, 1996, Cell & Developmental Biology, USA, 7: 23–29.*

Greider et al., Telomeres and Telomerase in Cell Senescence and Immortalization, 1996, Cellular Aging and Cell Death: 123–138.

Greider, Carol W., Telomere Length Regulation, 1996, Annu. Rev. Biochem, 65: 337–365.

Nugent et al., Cdc 13p: A Single–Strand Telomeric DNA–Binding Protein with a Dual Role in Yeast Telomere Maintenance, 1996, Science, 274: 249–252.

Virta–Pearlman et al., Est1 has properties of a single–stranded telomere end–binding protein, 1996, Genes & Development, 10: 3094–3104.

Wrigth et al., Experimental elongation of telomeres extends the lifespan of immortal x normal cell hybrids, 1996, The EMBO Journal, England, 15: 1734–1741.

Makarov et al., Long G Tails at Both Ends of Human Chromosomes Suggest a C Strand Degradation Mechanism for Telomere Shortening, 1997, Cell, 88: 657–666.

Steensel et al., Control of telomere length by the human telomeric protein TRFI, 1997, Nature, 385: 740–743.

Planck et al., Modulation of hnRNP A1 protein gene expression by epidermal growth factor in Rat–1 cells, 1988, Nucleic Acids Research 16: 11663–116673.

* cited by examiner

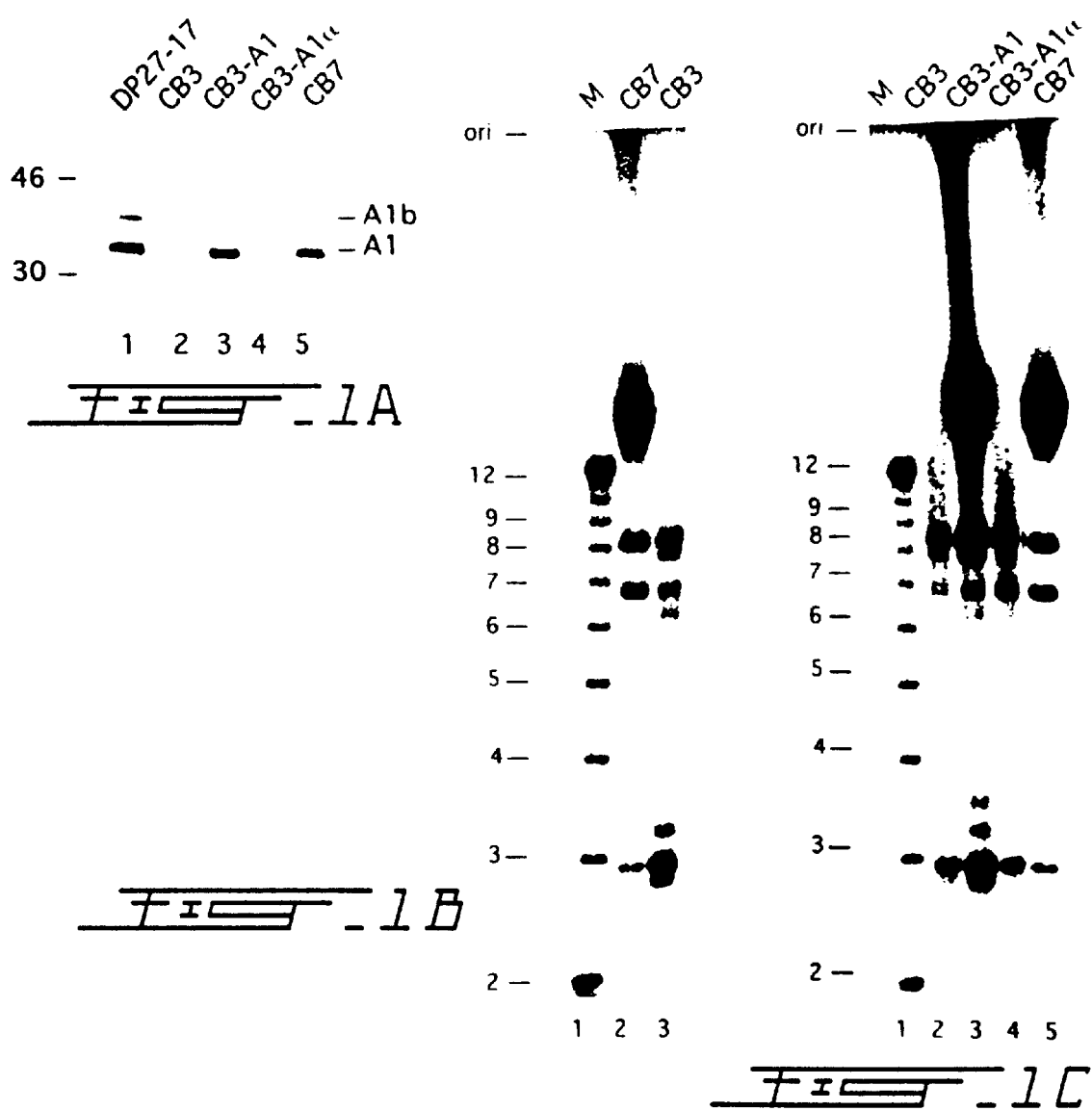

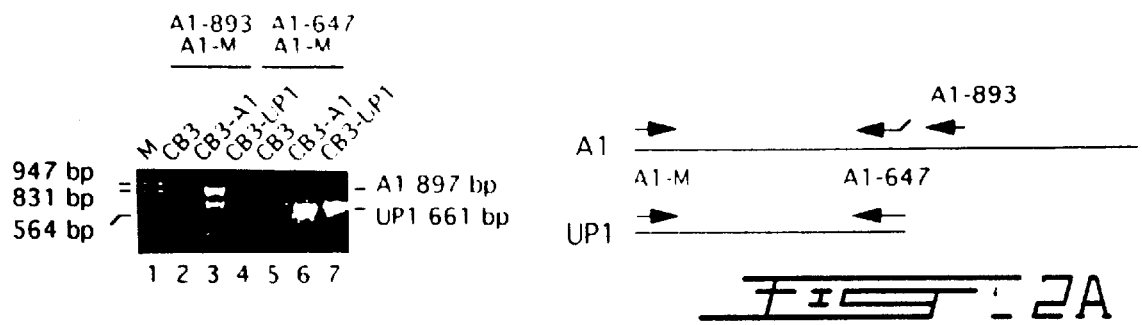
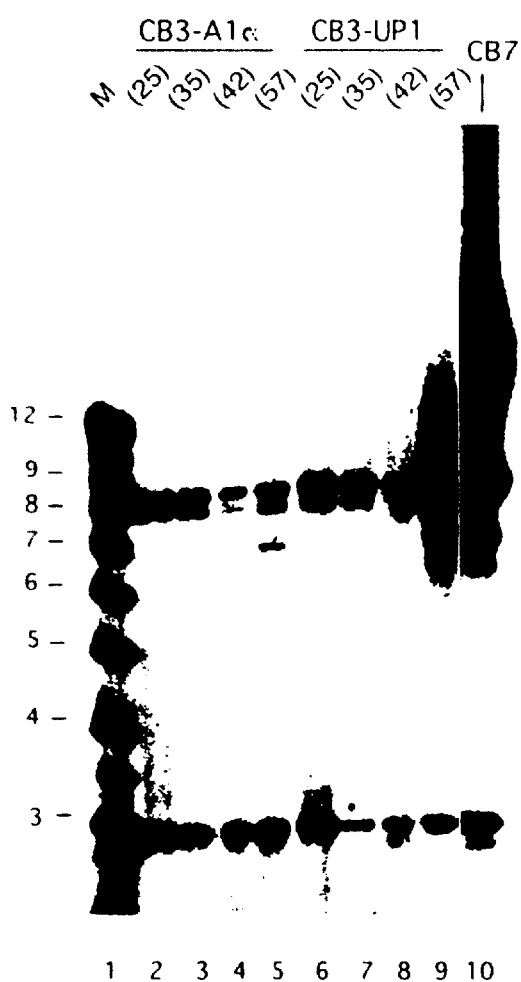
FIG. 2A
FIG. 2B

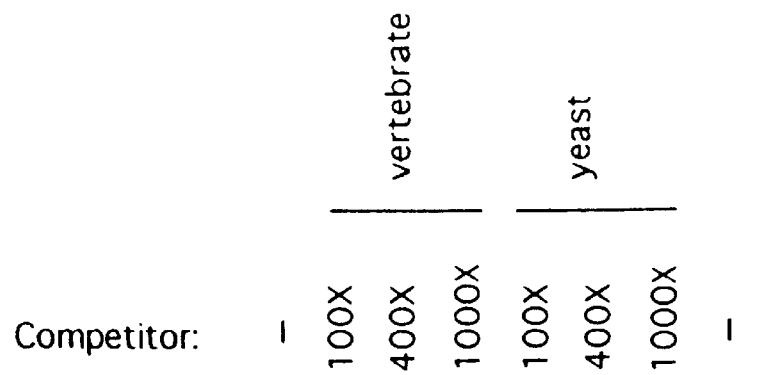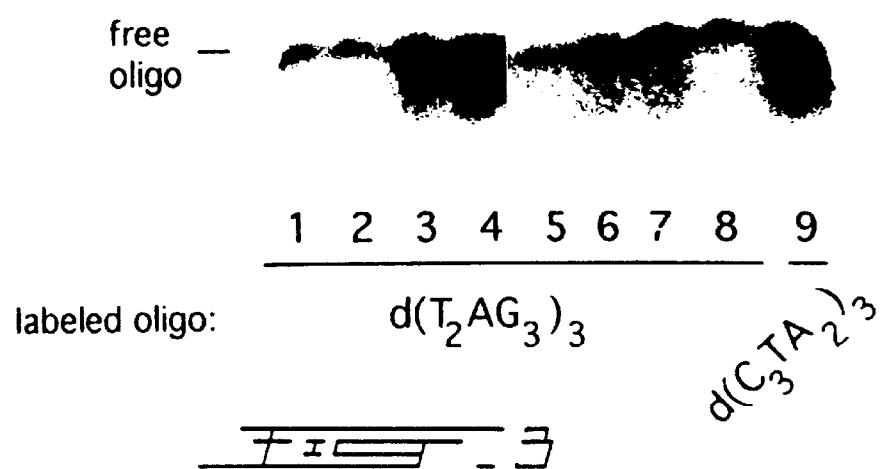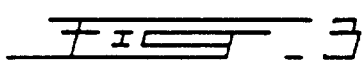

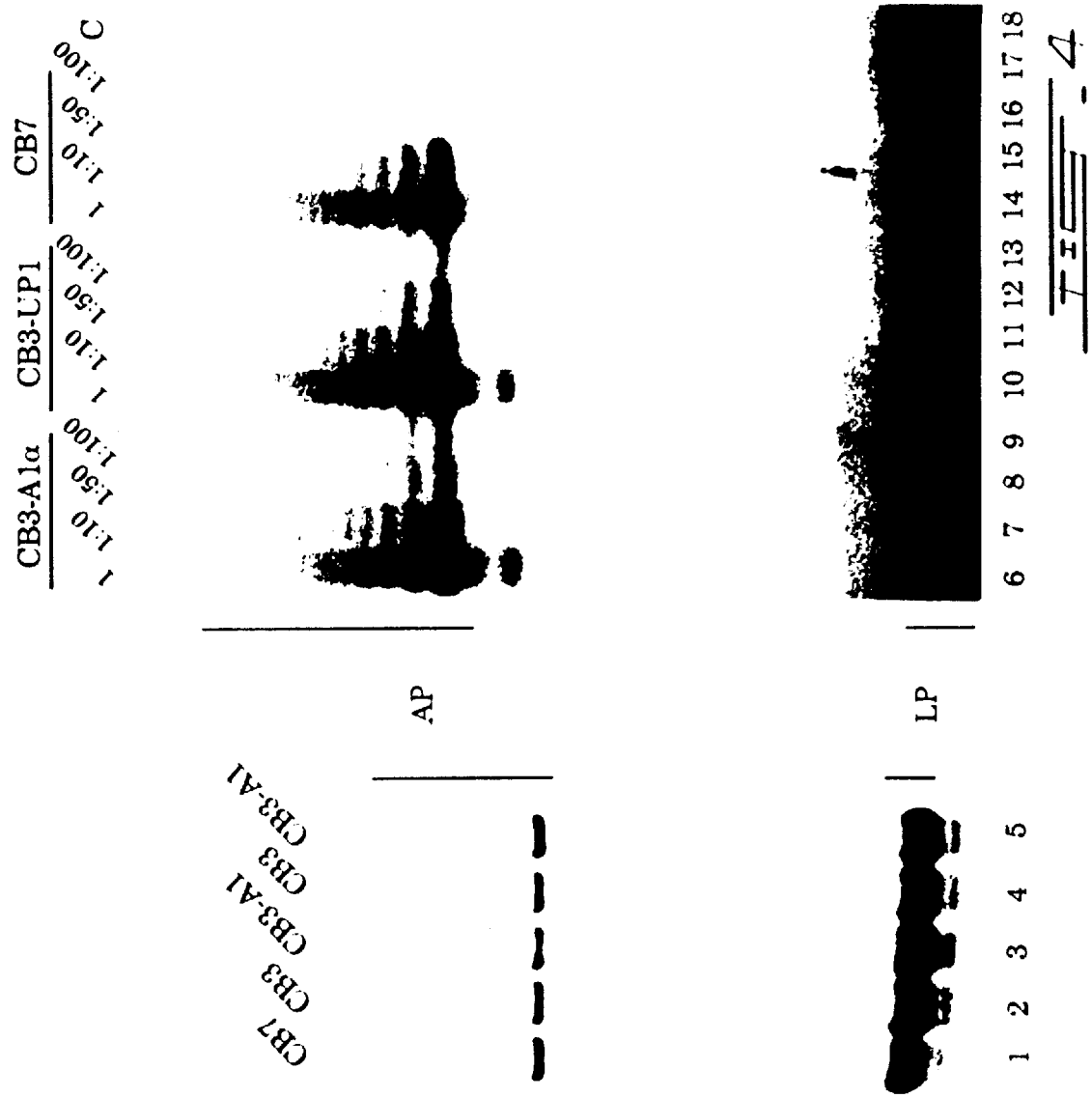

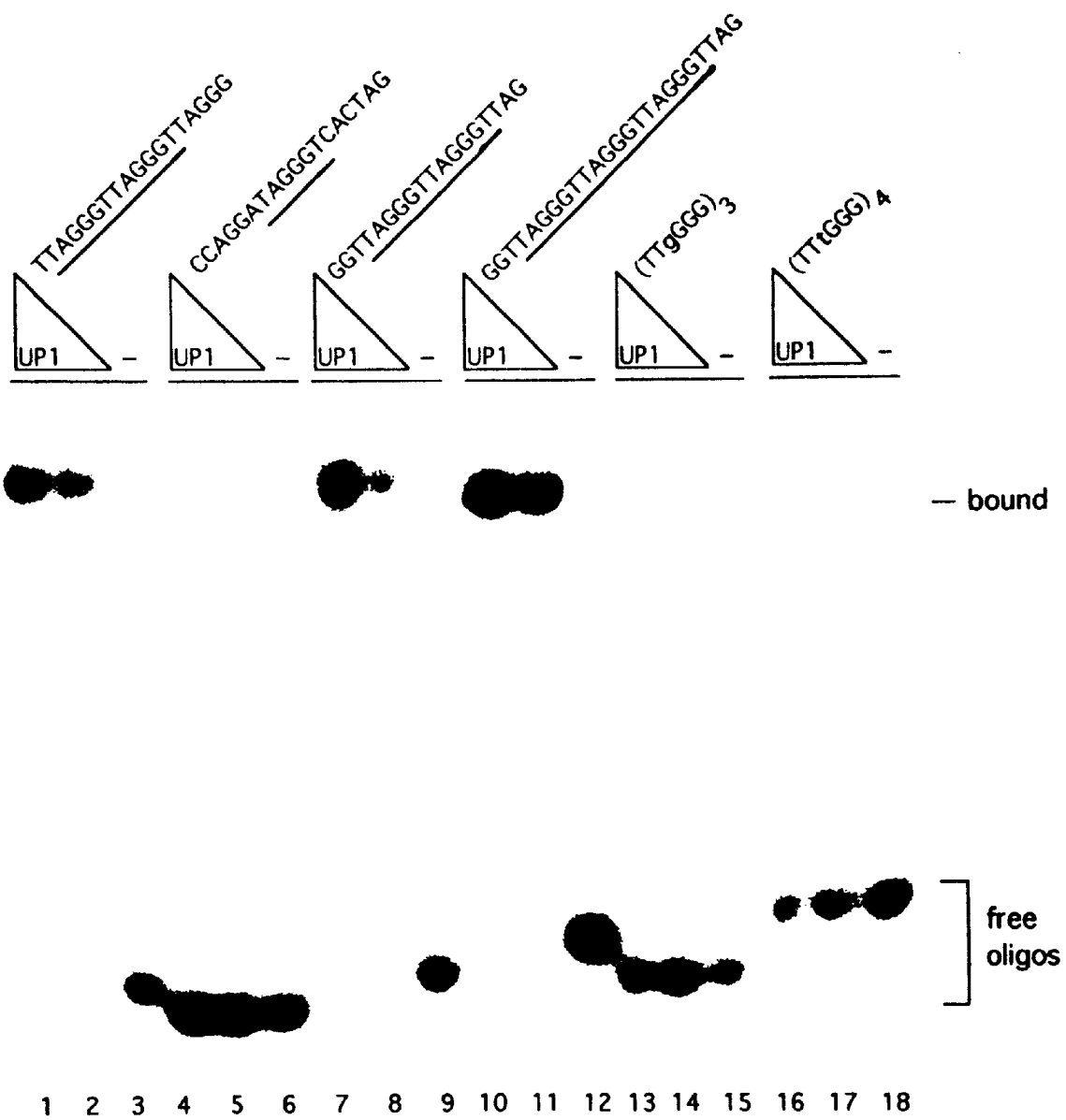
SPECIFIC INTERACTION OF
GST-UP1
WITH TELOMERIC REPEATS

COMPOSITION AND METHODS FOR MODULATING THE LENGTH OF TELOMERES

This Application is a 371 of PCT/CA97/00471 filed Jun. 30, 1997 and also claims benefit of 60/020,956 filed Jul. 1, 1996.

FIELD OF THE INVENTION

The present invention relates to the length of telomeres and to their effect on proliferation and senescence in cells. More particularly, the present invention relates to hnRNP A1, UP1 or derivatives thereof to maintain or alter the length of telomeres in cells. The present invention also relates to methods and compositions for increasing or decreasing the proliferative capacity of cells and to delay or precipitate the onset of senescence. The invention further relates to pharmaceutical, therapeutic and diagnostic reagents which relate to telomere length and/or to the modulations thereof.

BACKGROUND OF THE INVENTION

Telomeres are the DNA structure at the ends of the chromosomes of eukaryotes, including human, and are comprised of variable lengths of double strander repeats terminating with single-stranded repeats originally identified in yeast and protozoa (Makarov et al., 1997, Cell 88:657–666).

Review articles concerning telomeres include Greider, 1996, Ann. Rev. Biochem. 65:337 and Zakian, 1995, Science 270:1601. Relevant articles on various aspects of telomeres include Cooke and Smith, 1986, Cold Spring Harbor Symp. Quant. Biol. 51:213; Morin, 1989, Cell 59:521; Blackburn et al., 1989, Genome 31:553; Szostak, 1989, Nature (London) 337:303; Gall, 1990, Nature (London) 344:108; Henderson et al., 1990, Biochemistry 9:732; Gottschling et al., 1990, Cell 630:751; Harrington et al., 1991, Nature (London) 353:451; Muller et al., 1991, Cell §67:815; Yu et al., 1991, Cell 67:823; Gray et al., 1991, Cell 67:807; de Lange, 1995, "Telomere Dynamics and Genome Instability in Human Cancer", E. Blackburn and C. W. Greider (eds), in Telomeres, Cold Spring Harbor Laboratory Press, pp. 265–293; Rhyu, 1995, J. Natl. Cancer Inst 87:884; Greider and Harley, 1996, "Telomeres and Telomerase in Cell Senescence and Immortalization", in Cellular Aging and Cell Death, Wiley-Liss, Inc., pp. 123–138. Other articles of some relevance include Lundblad et al., 1989, Cell 57:633 and Yu et al., 1990, Nature (London) 344:126.

Maintenar the integrity of teloees is essential for cell suival (Muller, 1938, The Collectirg Net 13:181–195; Sandell et al., 1993, Cell 75:729–739). The proliferative potential of cells has been correlated with alterations in the length of these tandemly repeated sequences (Zakian, 1989, Ann. Rev. Genet 23:579–604; Counter et al., 1992, EMBO J. 11:1921–1929).

The finite replicative capacity of normal human cells, e.g., fibroblasts, is characterized by a cessation of proliferation in spite of the presence of serum growth factors. This cessation of replication after a maximum of 50 to 100 population doublings in vitro is referred to as cellular senescence. See, Goldstein, 1990, Science 249:1129; Hayflick and Moorehead, 1961, Exp. Cell Res. 25.585; Hayflick, 1985, ibid., 37:614; Ohno, 1979, Mech. Aging. Dev. 11:179; Ham and McKeehan, 1979, "Media and Growth Requirements", W. B. Jacoby and I. M. Pastan (eds), in Methods of Enzymology, Academic Press, NY, 58:44–93. The replicative life span of cells is inversely proportional to the in vivo age ofthe donor (Martin et al., 1979, Lab. Invest. 23:86; Goldstein et al. 1969, Proc. Natl. Acad. Sci. USA 64:155; Schneider and Mitsui, 1976, ibid, 73:3584) and is therefore suggested to reflect in vivo ageing on a cellular level.

Cellular immortalization (unlimited life span) may be thought of as an abnormal escape from cellular senescence (Shay et al., 1991, Emp. Cell Res. 196:33). Normal human somatic cells appear to be mortal, i.e., have finite replication potential. In contrast, the germ line and malignant tumor cells are immortal (have indefinite proliferative potential). Human cells cultures in vitro appear to require the aid of transforming oncoproteins to become immortal and even then the frequency of immortalization is $10^{-6}$ to $10^{-7}$ (Shay et al., 1989, Emp. Cell Res. 184:109). A variety of hypotheses have been advanced over the years to explain the causes of cellular senescence. One such hypothesis proposes that the loss of telomec DNA with age, eventually triggers cell cycle exit and cellular senescence (Zakian, 1989, Ann. Rev. Genet 23:579–604; Harley et al. 1990, Nature (London) 345:458–460; Hastie et al., 1990, Nature (London) 346:866–868; Allsopp et al., 1992, Proc, Natl. Acad. Sci. USA 89:10114–10118; Counter et al., 1992, EMBO J. 11:1921–1929).

Human primary fibroblasts in culture enter crisis after a precise number of cell division associated with gradual telomere shortening, at which point all the cells die (de Lange, 1994, Proc. Natl. Acad. Sci. USA 91:2882–2885). Mouse primary fibroblasts have longer and/or more stable telomeres and display a similar behavior when cultured in vitro (Prowse and Greider, 1994, Proc. Natl. Acad. Sci. USA, 92:4818–4822). However, after crisis, primary mouse cells in culture spontaneously immortalize with a frequency of $10^{-6}$, possibly because longer telomeres facilitate the growth of mutant cells (de Lange, 1994, Proc. Natl. Acad. Sci. USA 91:2882–2885).

It should be noted, as mentioned above, that other hypotheses have been advanced to explain senescence and that there is yet to be a consensus or a universally accepted hypothesis therefor. Previously, the causal relationship between telomeres and cancer/ageing/senescence had been built entirely on correlative studies.

Recent data has shown that telomeres play a direct role in cell senescence and transformation. Indeed, Wright et al., 1996, EMBO J. 15:1734–1741, using telomerase-negative cells which have limited life span in tissue culture, have shown that the introduction of oligonucleotides carrying telomeric repeats causes telomere elation and increases the proliferative capacity of these cells. Moreover, the authors state that "previous studies had shown a remarkable correlation between telomere length and cellular senescence. The present results provide the first experimental evidence for a true causal relationship between telomere length and a limited proliferative capacity". Feng et al., 1995, Science 269:1236–1241 showed that human cell line (HeLa) transfected with an antsense telomere RNA, loose telomeric DNA and begin to die after 23–26 cell doublings. The author claim that "the results support the hypothesis that telomere loss leads to crisis and cell death once telomeres are shortened to a critical length".

The postulated link between senescence/proliferation of cells and telomere length has led to therapeutic and diagnostic methods relating to telomere length or to telomerase, the ribonucleoprotein enzyme involved in the synthesis of telomeric DNA. PCT Publication No. 93/23572 describes oligonucleotide agents that either reduce the loss of telomeric sequence during passage of cells in vitro, or increase telomeric length of immortal cells in vitro. The same type of approach is also taught in PCT Publication No. 94/13383 and U.S. Pat. No. 5,484,508 which refer to methods and compositions for the determination of telomere length and telomerase activity, as well as to methods to inhibit telomerase activity in the treatment of proliferative diseases. Methods to increase or decrease the length of telomeres through an action on telomerase is also taught. The agents which are shown to reduce telomere loss of telomere length during proliferation are oligonucleotides which promote synthesis of DNA at the telomere ends, as well as telomerase.

PCT Publication No. 95/13383 discloses a method and compositions for increasing telomeric length in normal cells so as to increase the proliferative capacity of the cells and to delay the onset of cellular senescence. PCT Publication No. 96/10035 teaches that telomere length serves as a biomarker for cell turnover. Furthermore, it discloses that measuemert of telomere length can be used to diagnose and stage cancer and other diseases as well as cell senescence.

Heterogeneous nuclear ribonucleoprotein particles (hnRNP) proteins are abundant proteins mammalian cells, of which the A to U members have been best characterized due to their RNA binding properties (Dreyfuss et al., 1993, Ann. Rev. Biochem. 62:289). There are over 20 such hnRNP proteins in human cells. The best characterized hnRNP protein so far is the hnRNP A1 protein which has been shown to be involved in alternative RNA splicing (Mayeda et al., 1992, Cell 68:365–375; Yang et al., Proc. Natl. Acad. Sci. USA. 91:6924–6928). Indeed, the hnRNP A1 protein has high affinity for RNA in vitro (Bird and Dreyfuss, 1994, EMBO J. 13:1197–1204). UP1 is a proteolytic product derived from hnRNP A1 (Riva et al., 1986, EMBO J. 5:2267–2273). UPI has no activity in alternative splicing in vitro (Mayeda et al., 1994, EMBO J. 13:5483–5495). In vitro experiments have shown that hnRNP A1 binds to oligonucleotides containing vertebrate 3' splice site sequences (Buvoli et al., 1990, Nucl. Acids Res. 18:6595). The DNA version of 3' splice site sequences share some similarity with vertebrate telomeric repeats (Ishikawa et al., 1993, Molec. Cell. Biol. 13:4301–4310). In vitro data concerning hnRNP A1 (UP1) can be summarized as follows: (1) A1 binds to DNA oligonucleotides carrying 3' splice site sequences which contain TTAGGT(Buvoli et al., 1990, Nucl. Acids Res. 18:6595); (2) UP1 is part of complexes assembled on oligonucleotides carrying telomeric repeats (TTAGGG)n (Ishikawa et al., 1993, Molec. Cell. Biol. 13:4301–4310), indicating that A1 and/or UP1 "could perhaps" bind to chromosome telomeres. However, this in vitro result is not yet correlated with in vivo data and cannot demonstrate th direct interaction of A1 and/or UP1 with telomeric repeats in the complex formed. Moreover, the oligonucleotides used in the expement which carry telomeric repeats also resemble the 3' splice site oligo used by Buvoli et al., 1990, Nucl. Acids Res. 18:6595. This could mean that (UP1) binds to 3' splice site sequences and that the telomeric sequence happens to resemble a 3' splice site (DNA version), and (3) Bird and Dreyfuss, 1994, EMBO J. 13:1197–1204 show that A1 binds to RNA and that the optimal sequence recognized by A1 resembles a 3' splice site and a 5' splice site. Although the optimal recognition sequence also resembles a telomeric repeat, the hypothesis that A1 might bind to telomeres appears to have been discarded. Models in which A1 binds to its preferred sequence in the context of an RNA molecule to modulate splicing, transport and possibly translation appear to be favoured (Bird and Dreyfuss, 1994, EMBO J. 13:1197–1204).

Proteins that bind telomeric repeats may be subdivided into two categories, those that bind double-stranded repeats and those that bind single-stranded repeats. See Lin, 1993, BioEssays 15:555. A number of proteins binding to double-stranded repeats have been characterized. These include RAP1 and TBFα from yeast, PPT in Physarum and TRF in mammals.

While TBFα and PPT do bind oligonucleotides containing telomeric sequences in vitro, there has been no demonstration that these proteins bind telomeres in vivo. RAP1, but not TBFα, influences the length of telomeres in yeast (Conrad et al., 1990, Cell 63:739). In mammals, it is noteworthy that TRF has been shown to bind to telomeres in vitro (Chong et al., 1995, Science 270:1663). Moreover, overexpression of TRF promotes a reduction in the length of telomeres while expessing a mutated form of TRF causes telomere elongation (van Steensel et al., 1997, Nature (London) 385:740 and de Lange W097/08314).

Proteins that can bind to single-stranded telomeric repeats in vitro include protein α and β of Oxytrichia and Stylonychia, a of Euplotes, MF3 of chicken and XTEF of Xenopus. There has been no demonstration that the vertebrate proteins MF3 and XTEF bind to telomeres in vivo and no suggestion that their expression influences the size of telomeres. The yeast NSR1, GBP2, cdc13/EST4 and EST1 proteins were shown to bind to single-stranded yeast telomeric DNA (Lin and Zakian, 1994, Nucl. Acids Res. 22:4906; Nugent et al., 1996, Science 274:249; Virta-Pearlman et al., 1996, Genes Dev. 10:3094). While NSR1 and GBP2 do not affect telomere length in vivo, mutant strains engineered not to exress cdc13p or to express mutated forms of EST1 undergo telomere attrition despite having wild-type amounts of telomerase activity (Nugent et al., 1996, Science 274:249; Virta-Pearlman et al., 1996, Genes Dev. 10:3094). A limited number of mammalian proteins, including hnRNP proteins, have been reported to associate with oligonucleotides carrying telomeric repeats (Ishikawa et al., 1993, Molec. Cell. Biol. 13:4301–4310; McKay and Cooke, 1992, Nucl. Acids Res. 20:6461–6464; de Lange, 1996, Seminars in Cell & Dev. Biol. 7:23–29; Sang et al., 1997, J. Biol. Chem. 272:4474–4482). Whether any of these proteins bind to single-stranded telomeric repeats in cells and affect telomere length in vivo has yet to be documented. In any event the observation that a protein binds to telomeric sequences in vitro cannot be considered predictive of a role on the size of telomeres in vivo.

There thus remains a need for reagents other than oligonucleotides and telomerase that can influence the length of telomeres in cells and for methods to increase or decrease the proliferative capacity of cells and to delay or precipitate the onset of senescence. The present invention seeks to meet these and other needs as described below.

SUMMARY OF THE INVENTION

This invention concerns therapies or diagnostics associated with control of telomere length. The therapeutic strategies of the present invention include reducing the rate of the absolute amount of telomere length loss during cell proliferation, thereby providing for the postponement of cellular senescence and reducing the level of chromosomal fusion and other chomosomal aberrations. In addition, the activity of hnRNP A1 UP1 or derivatives thereof, may be used to control diseases associated with cell immortalization, such as neoplasia.

The invention also relates to the determination of cellular status by analysis of telomere length and level of hnRNP A1/UP1 and derivatives thereof. Assays are performed to provide useful information on the relative age and remaining proliferative capability of a wide variety of cell types in numerous tissues. The binding activity and/or level of A1 and more preferably UP1 is used as a marker for diagnosing and staging neoplasia.

Since a trypsin-like protease is thought to be involved in the conversion between hnRP A1 to UP1 (Pandolfo et al. 1985, Nucl. Acids Res. 13:6577–6590), the present invention also concerns this trypsin-like protease as a target for influencing the length of telomeres. In additian this protease (absolute amounts or activity) can also be used as a marker of cellular capacity for proliferation of the cell and for diagnosing and staging neoplasia.

The applicant has determined that cells that do not contain detectable amounts of hnRNP A1 have drastically shortened telomeric repeat length as compared to cells that contain normal levels of hnRNP A1. The applicant has also determined that restoring hnRNP A1 expression in hnRNP A1-deficient cells promotes a gradual increase in the length of telomeres. Moreover, the applicant has also determined that UP1, a proteolytic product of hnRNP A1 which has lost its activity in alternative splicing (Mayeda et al. 1994, EMBO J. 13:5483), also promotes a gradual increase in the length of telomeres when expressed in hnRNP A1-deficient cells. Thus, the applicant is the first to provide data ta hnRNP A1 and its derivative, UP1, influence the length of telomeres, thereby ruling out an indirect role through alternative splicing but rather giving rise to a factor involved in telomere length biogenesis or maintenance. Prior to applicant's experiments reported herein, there was no consensus by those in the art that one could predict that such experiments would provide the data observed by applicant or that such manipulations would have therapeutic utility.

Telomere length is correlated to the life-span of a cell; by increasing telomere length, the ability of a cell to replicate is inceased; by decreasing telomere length, the ability of a cell to replicate is decreased. The hnRNP A1 and UP1 fragments or mutated versions thereof, are used to forestall and reverse cellular senescence in the treatment of diseases such as age-related diseases (as examples but not limited to Alzheimer's disease, Parkinson's disease, Huntington's disease, stroke, osteoporosis and atherosclerosis) The method can be used to generate cells with high proliferative capacity for transplantation purposes (as example but not limited to cell therapy). As well, nonlimiting examples thereof include the treatment of AIDS, anemia, leukaemia and lymphoma. The method can also be used to prevent cellular senescence of cultured cells from different origin including, while not being limited to, embryonic stem cells and foetal stem cells and in addition it is useful in tissue-culture techniques and as a disease prevention method. UP1 fragments or mutated versions therefore are used in treatment of tumors to reduce the size of telomeres. This method can be used to control disease associated with cell immortality such as neoplasia (cancer) and proliferative diseases caused by infection. with pathogenic organisms. Mutated versions compete with endogenous hnRNP A1 and fragments involved in maintaining stable telomeres and result in decreasing length of telomeres causing genetic instability and cell death. By increasing the proliferative activity of totipotent or pluripotent cells, cells of any particular type can be generated and amplified. The increased proliferative activity can also be applicable to hybridomas produced from mammalian cells, preferably mouse and human cells. The method is applicable to all types of neoplasia (cancer) in contraindication to telomerase-based approaches which may not be applicable to certain types of tumors that have no detectable levels of telomerase activity.

Thus, in a first aspect, the present invention features a method to modulate the size of telomeres comprising the use of an effective amount of hnRNP A1, UP1, fragments of derivatives of hnRNP A1 or fragments and derivatives of UP1 or of the protease involved in the conversion of hnRNP A1 into UP1.

In a related aspect, the invention features a method for treatment of a condition associated with an increase rate of proliferation of a cell, e., telornere repeat loss associated with cell proliferation. The method involves administering to the cell a thrapeutically effective amount of hnRNP A1, UP1, fragments of derivatives of hnRNP A1 or fragments and derivatives of UP1 or of the protease involved in the conversion of hnRNP A1 into UP1 to reduce loss of telomere length within the cell during proliferation. Such agents are especially applicable to conditions related to increased cell proliferation.

By "increased rate of proliferation" of a cell, it is meant that a cell has a higher rate of cell divisions compared to normal cells of that cell type, or compared to normal cells within other individuals of that cell type. Examples of such cells but not limited to these, include the $CD4^+$ cells of HIV-infected individuals, connective tissue fibroblasts associated with degenerative joint diseases, age-related muscular degeneration, astrocytes associated with Alzheimer's Disease and endothelial cells associated with atherosclerosis. In each case, one particular type of cell or a group of cells is found to be replicating at an increased level compared to surrounding cells in those tissues, or compared to normal individuals, e.g., individuals not infected with the HIV virus. Thus, the invention features administering to those cells an agent which reduces the loss of telomere length in those cells while they proliferate. The agent itself need not slow the proliferation process, but rather allow the proliferation process to continue for more cell divisions than would be observed in theabsence of the agent. The agent may also be useful to slow telomere repeat loss ouTin during normal aging, and for reducing telofere repeat loss while e o cell number ex vivo for cell-based therapies. The agent could thus simply stabilize telomere length.

It should be understood that fragments and derivatives of hnRNP A1 or UP1, useful in modulting the lengh of telomeres, can be readily identified by those of ordinary skill in the art using routine screening procedures. For example, a particular cell having a known telomere length is chosen and allowed to proliferate and the length of telomere is measured during proliferation. Analysis of telomere length in cells expressing different derivatives or fragments can be identified using methods described below or other methods known to a person of ordinary skill Non-limiting examples of such derivatives and fragments comprise hnRNP A1 in vitro mutagenized in the portion which is absent in UP1, and mutations such as deletions, insertions, fusions and the like of hnRNP A1 and UP1. The same principle applies to the trypsin-like protease converting hnRNP A1 into UP1. In this case, derivatives thereof can be tested in vitro (cultured cells) or in vivo by their indirect role on telomere length.

Herein, hnRNP A1 and UP1 are meant to designate the nucleic acid and/or the protein. It will be recognized by a person of ordinary skill whether the protein or nucleic acid fragment is intended.

In related aspects, the present invention features a pharmaceutical composition which include therapeutically effective amounts of hnRNP A1, UP1, fragments of derivatives of hnRNP A1 or fragments and derivatives of UP1 or the protease involved in the conversion between hnRNP A1 and UP1 and pharmaceutically acceptable buffers much as described below. These pharmaceutical compositions may include one or more of these inhibitors or agents and can be co-administered with other drugs. For example, AZT is commonly used for treatment of HIV, and may be co-administered with an agent of the present invention.

In another related aspect, the invention features a method for extending the ability of a cell to replicate. In this method, a replication extending amount of an agent which is active to reduce loss of telomere length within the cell is provided during cell replication. As will be evident to those of ordinary skill in the art, this agent is similar to that useful for treatment of a condition associated with an increased rate of proliferation of a cell. However, this method is useful for the treatment of individuals not suffering from any particular condition, but in which one or more cell types are limiting in that patient, and whose life can be extended by extending the ability of those cells to continue replication. That is, the agent is added to delay the onset of cell senescence characterized by the inability of that cell to replicate further in an individual. One example of such a group of cells includes lymphocytes present in patients suffering from Downs Syndrome (although treatment of such cells may also be useful in individuals not identified as suffering from any particular condition or disease, but simply recognize that one or more cells, or collections of cells are becoming limiting in the life span of that individual).

It is notable that administration of such inhibitors or agents is not expected to be detrimental to any particular individual. However, should gene therapy be used to introduce the agents of the invention into any particular cell population, care should be taken to ensure that the activity of that agent is carefully regulated, for example, by use of a promoter which can be regulated by the nutrition of the patient Thus, for example, the promoter may only be activated when the patient eats a particular nutrient, and is otherwise inactive. In this way, should the cell population become malignant, that individual may readily inactivate replication of the cell and cause it to become senescent simply by no longer eating that nutrient.

In a further aspect, the invention features a method for diagnosis of a condition in a patient associated with an elevated level of the trypsin-like protease activity responsible for converting hnRNP A1 into UP1 within a cell. The method involves determining the presence or amount of this protease or measuring its activity within the cells in that patient. Common methods can be used for this determination.

In yet a further aspect, the invention provides a means of increasing the frequency of immortalization of normal primary cells comprising the introduction therein of a nucleic acid segment encoding hnRNP A1, UP1 or fragments or derivatives thereof. An increased expression of hnRNP A1, UP1 or fragments or derivatives thereof should prevent telomere shortening and cell crisis.

A second aspect of the present invention features a method for treatment of a condition associated with an elevated level of telomerase activity and/or with longer and/or more stable telomeres within a cell. The method involves administering to that cell a therapeutically effective amount of an agent that reduces or destabilizes the length of the telomeres. Such agents comprise hnRNP A1, UP1, fragments or mutated versions of A1 or UP1 as well as fragments or mutated versions of the typsin-like protease involved in the conversion of A1 into UP1. The level of telomerase activity can be measured in accordance withe present invention or by any other existing method or equivalent method. Example of such conditions include neoplastic (cancerous) conditions, or conditions associated with the presence of cells which are not normally present in that individual, such as protozoan parasites or opportunistic pathogens. Administration of such an agent can be achieved by any desired mean well known to those of ordinary skill in the art.

Non-limiting examples of such agents also include antisense of hnRNP A1 or derivatives thereof. In addition, these agents include ribozymes which can target the degradation of A1 mRNA. Other types of agents encompassed by the present invention include ligands which are specific to hnRNP A1 or UP1. Non-limiting examples of such ligands include antibodies directed to hnRNP A1, UP1 or derivatives or fragments thereof.

By "elevated level" of such activity, it is meant that the absolute level of telomerase activity in a particular cell is elevated compared to normal cells in that individual or compared to normal cells in other individuals not suffering from the same condition. The same principle applies to an elevated level or an elevated activity of the trypsin-ike protease mentioned above, or to the activity of A1 or UP1 on the length of telomeres.

In addition, the term "Therapeutically effective amount" of an inhibitor is a well recognized phrase. The amount actually applied will be dependent upon the individual or animal to which treatment is to be applied, and will preferably be an optimized amount such that an inhibitory effect is achieved without significant side-effects (to the extent that those can be avoided by use of the inhibitor). That is, if effective inhibition can be achieved with no side-effects with the inhibitor at a certain concentration, that concentration should be used as opposed to a higher concentration at which side-effects may become evident If side-effects are unavoidable, however, the minimum amount of inhibitor that is necessary to achieve the inhibition desired should be used.

It should be undertood having now recognized that the protease converting hnRNP A1 into UP1 is a target for affecting the size of telomeres, inhibitors of protease activity could be screened in assays of the present invention or substitutes thereof, well known to a skilled artisan, to monitor and determine how such inhibitors of protease activity could decrease the length of telomeres in cells. Alternatively, inducers or stimulators of the protease activity could be identified.

By "inhibitor" is simply meant any reagent, drug or chemical which is able to inhibit the protease activity in vivo or in vitro. Such inhibitors can be readily identified using standard screening protocols in which a protease is placed in contact with a potential inhibitor and the level of UP1 versus hnRNP A1 and ultimately the length of the telomeres is measured in the presence or absence of the inhibitor or in the presence of varying amounts thereof. In this way, not only can useful inhibitors or stimulators be identified, but the optimum level of such an inhibitor or stimulator can be determined in vitro.

The therapeutic aspect of the invention is related to the now clear observation that the ability of a cell to remain immortal comprises the ability of that cell to maintain or increase the telomere length of chromosomes within that cell. Such a telomere length can be maintained by the presence of sufficient activity of the trypsin-like protease, or of hnRNP A1, UP1 or derivatives thereof. Thus, therapeutic approahes to reducing the potential of a cell to remain immortal focuses on the inhibition of protease activity or in the presence of an inhibitor of UP1 or hnRNP A1's role in maintaining the stability of telomeres in those cells in which it is desirable to cause cell death Example of such cells but not limited to include cancerous cells, which are one example of somatic cells which show increased length or stability of telomeres, and have become immortal The present invention now permits such cells to become mortal once more by a reduction in the size or the stability of the telomeres. As such, inhibition can be achieved in a multitude of ways as, for example, by providing inhibitors of protease, dominant negative mutants of hnRNP A1, of UP1, or of the protease, derivatives of these dominant negative mutants or antisense molecules of hnRNP A1, UP1 or of the protease converting the former into the latter.

The inhibitors may be used for treatment of cancers of any type non-limiting examples thereof, including solid tumors and leukemias, carcinoma, histiocytic disorders, leukemia, histiocytosis malignant, Hodgkin's disease, immunoproliferative small, non-Hodgkin's lymphoma, plasmacytomna, reticuloendotheliosis, melanoma and the like, osteosarcoma, rhabdomyosarcoma, sarcoma, neoplasms, and for any treatment or of all other conditions in which cells have become immortalized.

By "antisense molecules", it is meant nucleic acid fragments which are complementary to their target and eventually lead to an inhibition of the production of the protein encoded by this target These antisense can be small segments of nucleic acids or long ones. They can also comprise modifications which enhance their stability. The design of appropriate are molecules and derivatives thereof is well known to an artisan of an skill. These antisense against hnRNP A1 can be tested for their effects on telomere length in accordance with to present invention or other suitable methods.

In other cases, it is important to slow the loss of telomere sequences, in particular, cells in association with certain diseases (although such treatment is not limited to this, it can be used in normal ageing and ex vivo treatments). For example, some diseases are manifest by abnormal fast rate of proliferation of one or more particular groups of cells. One example of such a disease is AIDS, in which death is caused by the early senescence of CD4+ cells. It is important to note that such cells age, not because of abnormal loss of telomere sequences (although this may be a factor) but rather because the replicative rate of the CD4+ cells is increased such that telomere attrition occurs at a greater rate than normal for that group of cells (Lundblad and Wright, 1996, Cell 87:369). Thus, the present invention provides means to stabilize the length of telomeres. The applicant therefore is providing therapeutic agents which can be used in the treatment of such diseases, and in addition, the means of diagnostic procedures by which similar diseases can be detected so that appropriate therapeutic protocols can be devised and implemented.

Specifically, the loss of telomeres within any particular cell population can be reduced by provision of hnRNP A1, UP1, or derivatives thereof, the protease or stimulators of A1, UP1, and the like. These molecules can be provided within a cell in order to reduce telomere loss or to make that cell immortal. Those of ordinary skill in the art will recognize that other enzymatic activities may be used to enhance the lengthening of telomeres within such cells, for example, by providing certain viral sequences within a cell, non-limiting examples thereof enclude EBV and SV40. In addition, equivalent such molecules, or other molecules may be readily screened to determine those that will reduce loss of telomer or stabilize the length of same. Such screening may occur in vitro, and the therapeutic agents discovered by such screening utilized in Me above method in vivo. It should be understood that in some situations, in vitro assays such as gel shifts might be sufficient to assess the telomere length stabilizing activity of an agent. In other cases, the assessment of telomere length per se (as opposed to binding of an agent to the telomere) might have to be ascertained in cultured cells for example. The skilled artisan will be able to determine which assay (which are not limited to two listed above) is sufficient to determine the effect of the tested agent on telomere length.

With regard to diagnostic procedures, examples of such procedures become evident from the discussion above with regard to therapy. Since there is a direct correlation between the life span of an individual cell and the length of its telomere, these diagnostic procedures can be of great importance for predicting and evaluating the potential life span of any individual cell type and to follow telomere loss so that a revised estimate to that life span can be made with time.

In certain diseases, for example, the AIDS disease discussed above, it would of course be important to follow the telomere lenghth CD4+ cells. In addition, the recognition that the number of CD4+ are limiting in such individuals allows a therpeuroc protocol to be devised in which CD4+ cells can be removed from the individual at an early age when AIDS is first detected, stored in a bank, and then reintroduced into the individual at a later age when that individual no longer has the required number of CD4+ cells available. Thus, an individual's life can be extended by a protocol involving continued administration of that individual's limiting cells at appropriate time points. These appropriate points can be determined by following CD4+ cell senescence, or by determining the length of telomeres within such CD4+ cells (as an indication of when those cells will become senescent). In this way, rather than wait until a cell becomes senescent (and thereby putting an individual at risk of death) telomere length may be followed until the length is reduced below that determined to be pre-senescent, and thereby the timing of administration of new CD4+ cells can be optimized. In addition, the cells reintroduced into the patient could have been designed to have a longer life span, by providing agents that will stabilize or lengthen the size of the telomeres.

Thus, the diagnostic procedures of this invention include procedures in which telomere length in different cell populations is measured to determine whether any particular cell population is limiting in the life span of an individual, and then determining a therapeutic protocol to insure that such cells are no longer limiting to that individual. In addition, such cell populations may be specifically targeted by specific drug administration to insure that telomere length loss is reduced and/or stabilized, as discussed above.

Other objects features and advantages of the present invention will become apparent upon reading of the following non-restrictive description of te preferred embodiments thereof given by way of example only with reference to the accompanying drawings and from the claims.

BRIEF DESCRIPTION OF THE DRAWINGS

In the appended drawings:

FIG. 1 shows that hnRNP A1 expression Set telomere length (A) Western analysis of hnRNP A1 expression in CB3 cells and derivatives stably restored for A1 expression. Total proteins (5 μg) from various mouse erythroleukemic cells were separated by SDS/PAGE. Following transfer onto nitrocellulose, the monoclonal antibody 9H10 (Bird et al., 1994, EMBO J. 13:1197, kindly provided by G. Dreyfuss) was used to detect hnRNP A1 proteins by ECL (AmershamLife Sciences). DP27-17 (lane 1) and CB7 (lane 5) cells are mouse erythroleukaemic cell lines (Shibuya et al., 1983, Proc. Natl. Acad. Sci. U.S.A. 80:3721; Ben-David et al., 1991, Genes Dev. 5:908) that express normal levels of hnRNP A1 proteins. CB3 (lane 2) cells are deficient in hnRNP A1 expression (Ben-David et al., 1992, Mol. Cell. Biol. 12:4449; Yang et al., 1994, Proc. Natl. Acad. Sc. U.S.A 91:6924). CB3-A1 (lane 3) cells are CB3 cells that have been stably restored for hnRNP A1 expression, by infection with a recombinant retrovirus. Retroviral vectors were constructed by inserting the mouse A1 cDNA (Ben-David et al., 1992, Mol. Cell. Biol. 12:4449) into the EcoRI site of pMSLV, a retroviral vector containing the neomycin resistance gene driven by the pgk promotor (Hawley et al., 1992, J. Exp. Med. 176:1149).Recombinant retroviral vectors were transfected into GP+-A86 cells (Hawey et al., 1992, J. Exp. Med. 176:1149).Following selection in the presence of G418, viral stocks were harvested and their titers determined. CB3 cells were then infected with each viral stock and pools of infected cells were selected in medium containing G418 (800 $\mu$g/ml for the first week and 400 $\mu$g/ml thereafter).Cells were seeded twice weekly at a 1:20 split ratio. CB3-A1a (lane 4) cells were produced by infection of CB3 cells with a retrovirus carrying the A1 cDNA in reverse orientation. The position of molecular weight marker is indicated at left; the respective cell lines from which the protein extract were prepared are indicated on the top of each lane; the positions of the A1 protein and its spliced isoform A1b are shown at right (B, C) Genomic DNA was extracted from mouse erythroleukaemic cells, digested with Hinfl and Rsal. For each lane, 5 $\mu$g of digested DNA was loaded onto the gel. The molecular size standard DNA was a mixture of $^{32}$P-end-labelled ladder DNA (GIBCO) and unlabeled HindIII-digested lambda DNA. To confirm the identity of the telomeric signals detected in CB7 and CB3 cells, genomic DNA was digested with the Bal31 exonuclease prior to treatment with restriction endonucleases. This treatment abolished the telomeric signals while preserving the detection of restriction fragments containing internal sequences repeats in the mouse genome (data not shown). The restricted DNA was separated on a 0.5% agarose gel and hybridized to the mammalian telomeric probe $^{32}$P-(TCCCTAA)$_3$. In panel C, the DNA from mock-infected CB83 cells or CB3 cells infected with the A1 or A1α viruses was analysed after 46 cell passages. The position and size (in kb) of molecular weight markers (M) are indicated (lanes 1 in panels B and C).

FIG. 2 shows Mat UP1 promotes telomere elongation in CB3 cells. (A) A1 and UP1 RNA expression in CB3, CB3-UP1 and previously produced CB3-A1α cells was monitored by RT-PCR following digestion of the RNA samples with DNase I. The position of the oligonucleotide primers is illustrated at right The amplified products were separated in a 1.5% agarose gel stained with ethidium bromide (left). The position and size of the amplified products are indicated as well as te position of molecular weight markers (M). The A1-893/A1-M primer set allows the detection of RNA transcribed only from the A1 construct since the UP1 construct does not contain sequns complementary to the A1-893 priner. However, RNAs generated fom both th A1 and UP1 contain sepuences complementary to the A1-647 primer, allowing the A1-647/A1-M primer set to detect both transcripts. (B) Genomic DNA was extracted from CB7 and CB3 cells infected with the A1α and UP1 viruses at different passages (number in parenthesis). The DNA was digested and hybridized to the telomeric probe as described in FIG. 1.

FIG. 3 shows that UP1 binds specifically to single-stranded vertebrate telomeric repeats. A gel shift assay (Virta-Pearlman et al., 1996, Genes Dev. 10:3094) was performed with purified recombinant GST-UP1 protein at 432 nM with 500 pM of end-labelled d(T$_2$AG$_3$)$_3$ (lanes 1–8) or d(C$_3$TA$_2$)$_3$ oligomer (lane 9). Unlabelled competitors were added at a molar excess and 1000 relative to the labelled vertebrate telomeric d(T$_2$AG$_3$)$_3$ oligomer. The competitor oligomers include the vertebrate telomeric oligomer (lanes 2–4) and the yeast telomeric GGGTGTGGGTGTGT-GTGGTGGG SEQ ID NO:3 oligomer (lanes 5–7).

FIG. 4 shows telomerase activity in A1-deficient, A1-and UP1 containing mouse cells. The cell lysates analysed were derived from mock-infected CB3 cells (lanes 2 and 4), CB3-A1 cells (lanes 3 and 5), CB3-A1α cells (lanes 6–9), CB3-UP1 cells (lanes 10–13) and CB7 cells (lanes 1 and 14–17). The TRAP assay was used to monitor telomerase activity (see Kim et al., 1994, Science 266:2011; Broccoli et al., 1995, Proc. Natl. Acad. Sci. U.S.A . 92:9082) was performed on mocknfected and viusinfected CB3 cells that had been passaged more than 40 times. Cell lysates were prepared using the CHAPS detergent lysis protocol. An equivalent of 10$^4$. cells was used in lanes 1–5 and lanes 6, 10 and 14. Serial dilutions of extracts were performed as indicated above the lanes. PCR products were resolved onto a 15% acrylamide non-denaturing gel. A control reaction was performed in the absence of cell extrad (C, lane 18). The positions of the labelled primer (LP) and the 6 bp-ladder of PCR products (AP) are shown.

FIG. 5 shows that $^{32}$P-labelled DNA oligonucleotides were mixed with Glutathione Sepharose 4B beads containing or lacking the GST-UP1 fusion protein. Following 5×1 ml washes in buffer containing 165 mM NaCl, the recovery of the labelled oligos was measured. The (TTAGGG)$_3$ oligonucleotide was recovered with the highest yield. A control experiment with plain beads yielded less that 10% of bound (TTAGGG)$_3$ oligonucleotide. A labelled DNA oligonucleotide containing the complementary sequence (CCCTAA)$_3$ was recovered at background level. An unrelated oligonucleotide of similar length was not significantly bound by GST-UP1. UP1 associated directly with telomeric repeats carrying the TTAGGG sequence. Gel-shift assays performed with mutated oligonudeotides indicate that UP1 binds specifically to (TTAGGG)$_3$ oligonucleotide.

DETAILED DESCRIPTION OF THE INVENTION

CB3 and CB7 cell lies were isolated from independent spleen colonies of a BALB/c mouse infected at birth with the Friend-Murine Leukaemia virus (Shibuya et al., 1983, Proc. Natl. Acad. Sci. 80:3721). Both CB3 and CB7 cells have sustained retroviral insertion events downstream of one of the two alleles encoding hnRNP A1 (Ben-David et al., 1992, Molec Cell. Biol. 12:4449). The second hnRNP A1 allele has been lost in CB3 cells (Ben-David et al., 1992, Molec. Cell. Biol. 12:4449). Consequently, CB7 cells contain nonmal levels of hnRNP A1 protein, whereas CB3 cells produce 200 to 500-fold less hnRNP A1 transcripts and no detectable hnRNP A1 protein (Ben-David et al., 1992, Molec. Cell. Biol. 12:4449; Yang et al., 1994, Proc. Natl. Acad. Sci. 91:6924) (FIG. 1A). The effect of the deficiency of hnRNP A1 on telomere length was investigated by Southern analysis (Harley et al., 1990, Nature (London) 345:458; Counter et al., 1992, ENMBO J. 11:1921). Genomic DNA from CB3 and CB7 cells was isolated, digested with Hinfl and Rsal, which do not cut in telomeric repeats, and separated on a 0.5% agarose gel. The dried gel was hybridized directly to a $^{32}$P-labeled telomeric probe d(CCCTAA)$_3$. Because the number of telomeric repeats varies on different chromosomes and between cells, the signals for the terminal restriction fragments (TRFs) appear as a smear. CB7 cells displayed an average TRF length of ~20 kb (FIG. 1B. lane 2). In contrast, te TRFs in CB3 cells were significantly shorter than 15 kb (FIG. 1B. lane 3).

To demonstrate that hnRNP A1 plays a role in telomere elongation the expression of hnRNP A1 in CB3 cells was stably restored. Restoration of hnRNP A1 expression was accomplished by engineering retroviral vectors carrying the murine hnRNP A1 CDNA under the control of the retroviral pomolor (see legend of FIG. 1). As a control, a retroviral vector containing the A1 cDNA in reverse orientation (A1α) was constructed. All retroviral vectors carried a copy of the neomycin gene under the control of the phosphoglucokinase promotor. Following transfecion of the recombinant retroviral DNAs into a packaging cell line, viral particles were harvested and used to infect CB3 cells. HnRNP Al expression was monitored after passaging the cells extensively in medium containing G418. Western analysis results indicate Mat hnRNP A1 expression was to normal levels in CB3-A1 cells (FIG. 1A, lane 3). No A1 protein was detected in G418resistant CB3 cells infected with the A1α virus (CB3-A1α; FIG. 1A, lane 4). Genomic DNA was isolated and analyzed for changes in the length of telomeres. infection of CB3 cells with the A1 virus led to a dramatic increase in the size of the TRFs, which averaged 20 kb after 46 cell passages (FIG. 1C, lane 3). In contrast, following infection with the A1α virus, cells grown for the same number of passages contained TRFs that remained comparable in size to those of the mock-infected CB3 cell culture (FIG. 1C, compare lane 4 with lane 2). This result was confirmed through an independent set of infections carried out on CB3 cells: A1 expression was associated with a gradual increase in the length of TRFs wich reached approximately 20 kb and remained stable thereafter despite continued passaging for more than one year (data not shown). As can be seen by comparing FIG. 1B, lane 3 with FIg. 1C, lane 2, some variation in the length of telomeres in the CB3 cell culture was noted during its propagation for prolonged periods, as seen with other immortal cell lines (Strahl et al, 1996, Mol. Cell. Biol. 16:53). However, the mean TRF lengths in CB3 cells always remained considerably shorter than the length of TRFs in CB3A1 cells derived from the same CB3 cell culture. infection of CB7 cells with the A1 virus did not lead to overexpression of hnRNP A1, and no change in telomere length was noted after continuously passaging the cells for more than one year in G418-containing medium (data not shown). A variety of assays that have included growth in medium with reduced concentration of serum and injection into mice et Fat changes in hrRNP A1 expression did not noticeably affect the transfomed properties of CB3 cells (data not Given that hnRNP A1 modulates alternative RNA Splicing (Yang et al., 1994, Proc. Natl. Acad. Sci. 91:6924; Mayeda et al., 1992, Cell 68:365; Cáeres et al., 1994, Science 265:1706), it is possible that hnRNP A1 influences splice site selection in an alternatively spliced pre-mRNA whose product affects telomere length. To address whether the effect of A1 on telomeres was dependent of its activity as an alternative splicing factor, we tested the effect of expressing UP1 in CB3 cells. UP1 is a proteolytic fragment of hnRNP A1 initially identified as a single-standed DNA binding protein (Riva et al., 1986, EMBO J. 5:2267; Herrick et al., 1976, J. Biol. Chem. 251:2124–2133; Cobianchi et al., 1988, J. Biol. Chem. 263:1063; Casas-Finet et al., 1993, J. Mol. Biol. 229:873). UP1 completely lacks activity in alternative splicing (Mayeda et al., 1994, EMBO J. 13:5483). A UP1 recombinant retrovirus was produced and used to infect CB3 cells. Briefly, the UP1 cDNA fragment was produced by PCR amplification of a mouse A1 cDNA clone using oligonucleotides A1 M [5'-AATT CTTTTGCTCGACGCTGCCGAG-3'; SEQ ID NO:4 the underlined sequence maps at the extreme 5' end of the murine A1 cDNA (Ben-David et al., 1992, Mol. Cell. Biol. 12:4449)], and A1-1647 [5-AATTCTGTCA GCGACCTCTCTGACTGGATGA-3'SEQ ID NO:5; the underlined sequene is complementary to the region encoding the carboxy-terminal domain of UP1]. PCR amplification leads to the inclusion of a stop codon immediately following the codon specifying the last amino acid in UP1. The 661 nt UP1 was subcioned, sequenced and inserted as an EcoRI fragment into the EcoRI site of pMSCV. Viral stocks were produced and used to infect CB3 cells as described earlier. Because the epitope recognized by the anti-A1 antibody is absent from the UP1 protein, a RT-PCR assay was used to monitor UP1 expression (FIG. 2A). Genomic DNA was isolated at regular intervals after infection and analyzed for changes in the length of TRFs. By comparison to a parallel infection of the same CB3 cell culture with the A1α virus (FIG. 2B, lanes 2–5), infection with the UP1 virus led to a gradual increase in the size of TRFs, the bulk of the fragments migrating in the 8–12 kb range after 57 cell passages (FIG. 2B, lanes 6–9). Further passages showed that the lengths of the telomeres kept on increasing. Indeed, at 86 passages the lengths of telomeres in CB3-UP1 cells was shown to comigrate with that of CB7 (data not shown). An increase in TRF size and hybridization intensity such as observed when hnRNP A1 (FIG. 1C, lane 3) or UP1 (FIG. 2B, lane 9) was expressed, was never observed in mock-infected CB3 cells or CB3 cells infected with the A1α virus. Thus, the increase in TRF size is specific to A1 and UP1 expression in CB3 cells and is not due to clonal variation.

Despite the fact that single-stranded oligomers carrying telomeric repeats are bound by A1 (Abdul-Manan et al., 1996, Biochemistry 35:3545; ibid., 1996, Nucleic Acids Res. 24:4063) and are assembled into UP1-containing complexes in HeLa extracts (Ishikawa et al., 1993, Mol. Cell. Biol. 13:4301), it is not yet known whether UP1 can interact directly with such repeats. Using a gel mobility shift assay, it is shown that purified recombinant UP1 binds to the single-stranded vertebrate telomeric oligonucleotide d(TTAGGG)$_3$ (FIG. 3, lanes 1 and 8). UP1 binding to the complementary oligonucleotide d(CCCTMA)$_3$ could not be detected (FIG. 3, lane 9). An excess of oligomer containing yeast telomeric repeats was considerably less efficient than cold d(TTAGGG)$_3$ at competing UP1 binding (FIG. 3, 2–8). These results suggest that UP1 binds preferentially to vertebrate telomeric repeats carrying TTAGGG repeats.

The decreased lengths of telomeric repeat tracts in CB3 cells could be a consequence of severely reduced or absent telomerase activity in these cells (Rogan et al., 1995, Mol. Cell. Biol. 15:4745; Bryan et al., 1995, EMBO J. 14:4240). To address whether changes in hnRNP A1/UP1 levels were associated with differences in telomerase activity, we performed a telomeric repeat amplification protocol (TRAP) (Kim et al., 1994, Science 266:2011; Broccoli et al., 1995, Proc. Natl. Acad. Sci. U.S.A . 92:9082) using extracts prepared from the A1-deficient, A1-,A1α-and UP1- expressing cells. Due to the mode of telomerase-medication repeat elongation, the TRAP assay typically yields a mixture of products with a 6 base-pair periodicity (Kim et al., 1994, Science 266:2011, Broccoli et al., 1995, Proc. Natl. Acad. Sci. U.S.A. 92:9082). No difference in the activity or the processivity of telomerase was observed between CB7, CB3 and virus-infected CB3 cells (FIG. 4).

The gradual changes in the telomeric repeat tracts following restoration of hnRNP A1 or UP1 expression in CB3 cells are reminiscent of a similar phenotypic lag associated with yeast telomere tract changes caused by Rap 1p overexpression (Conrad et al., 1990, Cell 63:739), by mutations in the EST1 and EST4/CDC13 genes (Nugent et al., 1996, Science 272:249; Lin et al., 1996, Proc. NaU. Acad. Sci. U.S.A 93:13760; Ludblad et al., 1989, Cell 57:633) or by certain RAP1 mutant alleles (Lustig et al., 1990, Science 250:549; Kyrion et al., 1992, Mol. Cell. Biol. 12:5159). HnRNP A1 does not share significant similarity with these and other yeast proteins that bind to single-stranded telomeric repeats or affect telomers length (Nugent et al., 1996, Science 272:249; Virta-Pearlman et al., 1996, Genes Dev. 10:3094;Greenwell et al., 1995, Cell 82:823; Morrow et al., 1995, Cell 82:831; Runge et al., 1996, Mol. Cell. Biol. 16:3094), nor with Tetrahymena (Collins et al., 1995, Cell 81:677) or Oxytricha (Hicke et al., 1990, Proc. Natl. Acad. Sci. U.S.A 87:1481; Gray et al., 1991, Cell 67:807) proteins that are either components of the telomerase or associate with telomeres in vivo. HnRNPA1 is also quite distinct from the human TRF protein which associates with double-stranded telomeric repeats (Zhong et al., 1992, Mol. Cell. Biol. 12:4834; Hanish et al., 1994, Proc. Natl. Acad. Sci. U.S.A 91:8861; Chong et al., 1995, Science 270:1663). Whereas members of the family of hnRNP proteins other than hnRNPA1 can associate with telomeric repeats in vitro (Ishikawa et al., 1993, Molec. Cell. Biol. 13.4301; McKay et al., 1992, Nucleic Acids Res. 20:6461), their presence in CB3 cells did not appear sufficient to prevent telomere shortening. Notably, the deficiency in hnRNP A1 was not associated with an absence or severely reduced telomerase activity, nor did restoring hnRNP A1 or UP1 expression affect telomerase activity in vitro. This result suggests that hnRNP A1/UP1 is not itself an obligatory part of the active telomerase complex nor is it required, at least in vitro, for substrate presentation to the telomerase. Our results raise the possibility that the proteolytic processing of A1 into UP1 may be part of the normal pathway that modulates oFe fi dAlin telomere biogenesis The binding of A1 or UP1 to single-band DNA carrying vertebrate TAGGGT repeats suggests possible mechanisms by which A1/UP1 can promote telomere elongation. HnRNP A1/UP1 may protect the exposed single-stranded tails from nudeolytic degradation. Because UP1 stimulates DNA polymerase a (Riva et al., 1986, EMBO J. 5:2267), UP1 binding to single-st telomeric DNA may also facilitate C-strand synthesis after telomerase elongation.

Telomere stabilization is essential for cell immortalization. Although telomerase activation has been associated with immoralization and cancer (Counter et al., 1992, EMBO J. 11:1921; Kim et al., 1994, Science 266:2011; Counter et al., 1994, Proc. Natl. Acad. Sci. U.S.A. 91:2900), immortalized and cancer cells lacking detectable telomerase activity have been described (Rogan et al., 1995, Mol. Cell. Biol. 15:4745; Bryan et al., 1995, EMBO J. 14:4240; Kim et al., 1994, Science 266:2011). Interestingly hnRNP A1 expression increases with the transition from the quiescent to the proliferative state (Le Stourgeon et al., 1977, Cold Spring Harbor Symp. Quant. Biol. 42:885 (1977); Planck et al., 1988, Nucleic Acids Res. 24:11663; Biamonti et al., 1993, J. Mol. Biol. 230:77). Moreover, whereas hnRNP A1 is expressed at high levels in germ cells, immortalized cell lines and tumors, hnRNP A1 expression is reduced in differentiated somatic cells and in senescent cells that sustain telomere attrition (Kamma et al., 1995, Exp. Cell Res. 221:187; Hubbard et al., 1995, Exp. Cell Res. 218:241; Zhang et al., 1997, Science 276:1268). Since variations in hnRNP A1 levels affect the structure of telomeres in vivo, it is possible that hnRNP A1/UP1 plays a role in modulating telomere structure during development, aging and neoplasia.

The present invention is described in further details, in the following non-limiting examples.

EXAMPLE 1

Method to Increase the Frequency of Immortalization of Normal Primary, Cells

The procedure envisioned to increase the frequency of immortalization of normal primary cells involves, in one embodiment, introducing recombinant DNA molecules carrying the hnRNP A1 gene or modified versions thereof into primary cells. Overexpression of A1 or the modified versions should prevent telomere shortening and prevent cell crisis. Preferably, UP1 or modified version thereof will be used.

Means of introducing recombinant material into eukaryotic cells are well-described and can be accomplished by viral infection, lipofection, electroporation, transfection, etc. Described below is the technique of viral infection which was used to restore hnRNP A1 expression in CB3 cells.

1. Production of A1 Recombinant Virus.

The viruses A1, A1b, and UP1 have already been generated. The A1, A1 b, and UP1 cDNAs have been inserted into the MSCV retroviral expression vector (Hawley et al. 1991, Leukemia Research 15:659-673) through standard cloning procedures. The retroviral vector that was used also contained a neomycin gene that confers resistance to the drug G418. Retroviral vectors can be constructed to contain other selectable marker genes that confer resistance to other drugs, for example hygromycin and puromycin.

a) 0.1 $\mu$g of each A1 cDNA insert (EcoRI fragment) was mixed with 0.1 $\mu$g of MSCV linearized at the EcoRI site. Ligation was performed with T4 DNA ligase and the mixture transformed into bacteria. Colonies were screened for the presence of inserts into MSCV and the orientation of the insert was determined by digestion with restriction endonucleases. These are standard and well-described procedures of cloning.

b) Recombinant DNA molecules are transfected into an ecotropic helper-free packaging cell line (GP+E-86; Markowitz et al., 1988. J. Virol. 62:1120) that will yield viruses capable of infecting mouse cells. Different packaging cell lines are now available. Some packaging cell lines will allow production of amphotropic viruses, i.e. viruses that can infect a variety of species (including human).

Following transfection, the transfected packaging cells were grown in the presence of G418 until G418-resistant colonies appeared. These colonies can be pooled or individually grown and screened for highest virus production.

The viral particles are harvested by changing culture media when the cells reach a confluence of 70–80%. A 4 ml of culture media without G41 8 is applied to cells in a petri dish of 1 ml and left 4–16h. Petri dishes are put on ice and the supernatant is transferred into tubes. The cells are centrifuged at 1800 rpm for 3 min. The supernatant is then transferred into a clean tube on ice. The supernatant can be stored at −80° C. in small aliquots (0.5 ml).

2. Cells

Viral infection with the aim of increasing viability can be accomplished in principle on any type of primary cells, including, but not limited to embryonic stem cells, hematopoietic stem cells, and neural-derived stem cells.

3. Infection

Infection of mouse cells (or any other mammalian species including human) is accomplished by, a) Removnng culture supernant of cells gron in petri dishes (ca: $10^6$ cells /100 mm petri dish);

b) Mix 0.5 ml viral supernatant +0.5 ml cold polybrene (100 µg/ml of PBS) in a cold tube;

c) Apply the viral solution to cells;

d) Incubate at 37° C. for 40 min, shaking every 10–15 min.;

e) Aspirate cell supernatant and rinse cells with media without G418;

f) 24 h later change the culture media with media contain in G418. Resistant colonies appear 10–14 days later.

It was have already shown that recombinant A1 viruses can infect a variety mouse cells incduding erythroleukaemic cells (CB3. DP28, DP27, CB7), neuroblastoma cells (N2a) and immortalized fibroblast cells (NIH3T3). From this point on, cells will be collected at regular intervals for analysis of telomeres (see section i) and expression of A1 proteins or derivatives (see section ii). It should be noted that the infected cells cannot produce viral particles since they lack the ability to make the viral components required for viral production, only the packaging cell lines have this ability.

EXAMPLE 2

Analysis of telomeric DNA

1) Extraction of DNA a) Cells were resuspended (<$10^7$ cells) in 0.4 ml buffer DNA-A in a 1.5 ml epperndof tube (Buffer A=10 mM Tris pH 7.5–8.0), 10 mM EDTA, 10 mM NaCl). An equal volume of buffer DNA-B (DNA-A plus 2% SDS) containig proteinase K (100 µg/ml) was added to the cells mixture. The mixture was incubated for 3 hours at 37° C., shaking occasionally. An equal volume of water-saturated phenol was added and mixed on the rotator for 10–20 min. Following a microfuge spin for 3–5 min. Mte aqeous phase was removed using a 1 ml pipette with the tip cut off the plastic tip to avoid shearing the DNA The extraction was repeated using phenol:chloroform:isoamyl alcohol (25:24:1). The aqueous phase was removed following centrifugation and a further extraction was carried out using chloroform: isoamyl alcohol (24:1). The aqueous phase was transferred to a clear tube and the NaCl concentration raised to 0.2M, with gentle mixing. Two volumes of absolute ethanol were slowly added, the tube was swirled gently until DNA begins to precipitate. The precipitated DNA is spooled onto the tip of a sealed glass micropipette. The spooled DNA is rinsed in 70% ethanol and absolute ethanol successively and allowed to dry. The glass tip is broken in an epperndorf tube containing water (ca. 100 µl for $10^6$ cells). The tube is placed on a shaker overnight to allow the DNA to dissolve and a spectrophotometric reading of the optical density at 260 mm of a 10–20 µl aliquot in 1 ml of water (1 O.D.=50 µg/ml) is performed.

2) Gel Assay

Five µg of DNA were digested with restriction enzymes appropriate for telomere analysis (ex Hinfl and Rsal). In a total volume of 20 µl the tubes were incubated for 3 h-overnight at 37° C., after the is incubation, 2 µl of glycol dye were added. These samples were loaded on a 0.5% agarose gel made in 0.5X TBE (10X TBE=216 g Tris-Base, 18.6 g $NA_2EDTA$, 110 g boric acid, $H_2O$ to 2 L) that was allowed to solidify for at least Ih. 0.5X TBE was poured over the gel such that it covered half the thiess of the gel. The gel was run at 50 volts for 1 h. When to dye has entered the gel, the gel was covered with 0.5X TBE and the voltage turned to no more than 30 for 17.5 h. After that period, the gel was placed onto 2 pieces of Whatmann paper and covered with Saran Wrap. The gel was dried at 60° C. for 30 min. The dried gel was placed in denaturing solution (1.515M NaCl, 0.5N NaOH) with gentle shaking for 15 min. The denaturing solution was removed and the gel soaked in neutralizing solution (1.515M NaCl, 05M Tris-HCl pH 8) with gentle shaking for 10 min. The gel was removed and placed in a plastic bag and 5 ml of hybridizing solution was added, an additional 20 ml of hybridizing solution containing the telomeric probe was added. The bag was sealed and allowed to incubate at 37° C. for 16 h. The hybridizing solution was removed and the gel submerged in 0.24×SSC (20×SSC= 350.6 g NaCl, 176.4 g sodium citrate, adjust volume to 2L with $H_2O$, adjust pH to 7.0) with shaking for 7 min. This was replaced with fresh 0.24×SSC, with shaking for 7 min. This washing step was repeated. The gel was removed and placed on Whatman paper and covered wiith Saran Wrap. The gel was exposed to X-ray film for 1 to 3 days.

Hybridizing solution (100 ml)=25 ml 20×SSC, 10 ml Deinhart's solution, 3 µof 100 µM ATP, 33 µl denatured salmon sperm DNA (10 mg/ml), 1 ml of 5 mM pyrophosphate/10 mM $Na_2HPO_4$.

3) Preparation of Telomeric Probe

The following was prepared: 5 µl containing 5 pmoles of $(C_3TA_2)_3$, oligonucleotide, 8 µl of T4 kinase buffer, 5 µl of γ-$^{32}$P-ATP (Amersham), 1 µl T4 kinase and 61 µl $H_2O$; and incubated at 37° C. for 30 min. 20 µl was used for each telomere gel hydbridization experiment.

EXAMPLE 3

Analysis of hnRNP A1 Expression

1) Cell LYSIS

5×$10^6$ cells were centrifuged and rinsed twice in PBS-A (10 g NaCl, 0.25 g KCl, 1.4 g $NA_2HPO_4$, 0.25 g $KH_2PO_4$, $H_2O$ to 4L). The cell pellet was transferred to a 1.5 ml tube and resuspended in 500 µPBS-A to which 500 µl of 2× Laemmli dye was added. This was boiled for 5 min and stored at −80° C. until used.

2) Gel Separation of Proteins

The above sample was boiled for a 3 min and 20 µl of protein mixture loaded onto 12.5% polyacrylame/SDS gel (PAGE). This was electrophoresed at 30 mA until the dye was 1 cm from the bottom. The gel was equilibrated in transfer buffer (25 mM Tss-Baseo 192 mM glycine, 25% methanol) for 30 min.

3) Western Detection

The gel was transferred to a nitrocellulose membrane using western transfer apparatus. The nitrocellulose paper was soaked for 1 h in 0.1% SDS and 0.5% dry milk. The anti-hnRNP A1 antibody (9B10; provided by G. Dreyfuss) was added to milk/SD solution (1:1000) and, allowed to react for 2 h at room temperature then, washed in TBST (10 mM Tri-base, 150 mM NaCl, 0.1% Tween-20) twice for 15 min each time. The anti-mouse peroxydase-linked antibody (Amersham) was added for 1 hour (10 µl of antibody for 10 ml of solution) and the nitrocellulose washed twice in TBST for 15 min each time. The ECL antibody detection kit (Amersham) was used.

EXAMPLE 4

Monitoring Cell Crisis

Uninfected cells (or cells infected with retroviral vector lacking A1) will begin to die after a period of time which may vary depending on the type of cells that is used. Visual inspection of tissue culture containers or staining with Trypan blue, which stains only dead cells, is sufficient to detect crisis occurring in cell culture. Cell senescence can also be monitored by staining for β-galactosidase activity at pH 6.0. This marker can be detected in senescent cells but is absent in young proliferating cells, immortalized cells and young cells made nondividing by serum deprivation (Dimri et al., 1995, Proc. Natl. Acad. Sci. USA 92:9363). Survival beyond the crisis stage in A1-infected cells will be monitored as above. In the case of mouse cells, an increase in the frequency of cell survival and continued cell division will indicate that crisis has been forestalled. In human cells, any cell survival and division beyond the stage of crisis will indicate that the crisis was overcome.

EXAMPLE 5

Therapeutic Applications

The therapeutic applications of this procedure are far-reaching and can be used to extend the life of primary cells that will be used for transplantation purposes (cell therapy) in cases of AIDS, and other hematopoietic or immunological diseases (lymphoma, leukaemia etc.). The extended growth of primary cells will increase the period of time in which the cells can be manipulated to correct other defects (ex: eliminate HIV viral DNA, correct mutations responsible for hemophilia, thallassemia, leukemia etc.).

This procedure is also applicable to age-related diseases which involve neural degeneration like Alzheimer's disease, Parkinson's disease, or other degenerative diseases like osteoporosis, atherosclerosis, etc . . . . In these cases, neuronal tissue (or other tissues) from the affected individual can be obtained, the recombinant A1 molecules or derivatives introduced into the cells, and the cells reintroduced into the individual. Expression of A1 (or derivatives) could extend the life of these cells and prevent or reduce the progression of the disease.

The constitutive expression of A1 (or derivatives) in various tissues could be envisionned to oonfer a protective effect against ageing. Thus, this procedure could be used as preventive therapy and be applied to individuals with a high-risk of developping an age-related disorder.

Extended growth beyond the crisis stage will also be a useful tool to improve our basic understanding of biological mechanisms involved in cell crisis, cell division and a variety of other basic questions that have so far been addressed only through the use of immortalized or transformed cells in culture.

EXAMPLE 6

Treatment of Cancer

Introducing into HeLa cells (cells derived from a human cervical carcinoma) a vector that programs the expression of an atisense molecule complementary to the RNA portion of Fe telomerase reduces telomerase activity, decreases the size of telomeres and brings the HeLa cells into crisis (cell death) (Feng et al., 1995, Science 269:1236). This demonstrates the potential of telomerase inhibition as a therapeutic approach for treating human cancer. Since A1 is essential for maintaining stable telomeres, blocking A1 action should promote telomere shortening (as seen in CB3 cells which lack A1 and have short telemeres). CB3 cells are growing erythroleukemia cells, thus in this case, telomeric alterations are not associated with cell death. This is likely due to the presence of other mutations in these cells that can overcome the absence of A1. Without being limited to a particular model, the loss of telomeres is most likely the beginning of a cascade of events that leads to cell death and any alterations in the expression of proteins or factors at any of each step leading to cell death may prevent cell death. CB3 cells have suffered a number of other retroviral insertion events and they do not express p53, a gene essential for apoptosis (cell death).

Different neoplastic cells may respond differently to alterations in the expression of A1. Preferably, UP1 or derivatives thereof will be used.

The antibodies of the present invention, specific for hnRNP A1/UP1 can also be used to promote telomeric shortening.

EXAMPLE 7

Altering A1 ExDression a) Expression of A1 antisense molecules may reduce the level of A1 protein in the cells which should lead to shorter telomeres and eventually cell death.

b) Expression of mutated A1 or UP1 proteins may achieve the same result as above. Mutations in the RRM1 or the RRM2 regions of the A1 protein modify the properties of A1 binding to nucleic acids (Mayeda et al., 1994, EMBO J. 13:5483). Introducing into neoplastic cells a vector that allows the overexpression of a mutated A1 or UP1 may lead to a reduction of normal A1/UP1 molecules (through feedback inhibition on the endogenous A1 gene via translational regulation for example). The reduction in normal A1/UP1 proteins could then result in abnormal protection of telomeres which will decrease in size until cancer cells enter into crisis and die. Mutations can be introduced elsewhere to interfere with putative interactions with other factors thus competing with the normal action of A1/UP1. This will also lead to telomere shortening and cell death. Another way to produce dominant negative mutants of UP1 is to insert additional unrelated domains (e.g. GST, lac Z) at the $NH_2$- or COOH - terminus of UP1. Such bulky domains may not interfere with UP1 binding to telomeres but may interfere with the interaction of UP1 with other nuclear components and may prevent presentation of telomeres to the telomerase or may prevent the sequestering of telomeres to specialized nuclear structures, thus promoting rapid telomere attrition.

Based on the above results, generating transgenic mice exressing UP1 is potentiated. The choice of UP1 is preferred since this form does not intedere with alternative splicing, at least in vitro (Mayeda et al., 1994, EMBO J. 13:5493-95). Moreover, because hnRNP A1 is involved in at least two distinct molecular processes, the effects of aftering A1 expression in whole animals are unpredictable. Changes in the exprssion of A1 may be lethal or cause multiple defects due to one or several of te biological functions of A1. Transgenic animals will be generated by programming UP1 expression through different promotors including the MMTV promotor which allows to target tissue-specific expression in mammnary glands. A constitutive promotor (β-actin) will be used to drive UP1 expression in all tissues. An increase in the tissue-specific or general expression of UP1 should promote the formation of abnormally long and stable telomeres. Telomere elongation may be associated with a greater protection against cancer by keeping in check genomic instability. Alternatively, it may offer a selective growing advantage on cells that express oncogenes or mutated anti-oncogenes. The consequence of alterations in telomere structure on embryonic development (viability and incidence of gross abnormalities), genomic instability (gross chromosomal abnormalities determined by karyotype analysis and rate of spontaneous mutation in a reporter gene), tumor occurrence and susceptibility to mutagenic or tumorigenic agents (e.g. radiation), growth rate and frequency of spontaneous immortalization of primary fibroblasts will be followed. The effect of UP1 expression on tumor development will be further verified by performing crosses between MMTV/UP1 transgenic animals and syngenic MMTV/neu transgenics (Jackson Labs., Maine), a strain that displays a high incidence of mammary tumors.

To increase the relevance of this study to humans, it is proposed to cross UP1 transgenics (*M. musculus* strains) with the wild *Mus spretus* strain. *M. spretus* cells have smaller telomeres than *M. musculus* and disply a lower frequency of spontaneous immortalization. Following several backcrosses of UP1-transgenics with *Mus spretus*, a UP1 transgene expressed in the background of *Mus spretus* teloreres will be obtained. Experiments will be conducted as above to monitor the effects of UP1-mediated changes in telomere structure on cell senescence and the incidence of cancer.

EXAMPLE 8

UP1 Binds Directly to Single-stranded Telomere Repeats in Vitro

To address whether UP1 can bind directly and with specificity to telomeric repeats the following experiment was performed:

$^{32}$P-labelled DNA oligonucleotides were mixed with Glutathione Sepharose 4B beads containing or lacking the GST-UP1 fusion protein. Following 5×1 ml washes in buffer containing 165 mM NaCl, the recovery of the labelled oligos was measured. The (TTAGGG)$_3$ oligonucleotide was recovered with the highest yield. A control experiment with plain beads yielded less that 10% of bound TTAGGG)$_3$ oligonucleotide. A labelled DNA oligonucleotide containing the complementary sequence (CCCTAA)$_3$ was recovered at background level. An unrelated oligonucleotide of similar length was not significantly bound by GST-UP1. Thus, UP1 can associate directly with telomeric repeats carrying the TTAGGG sequence. Furthermore, gel-shift assays performed with mutated oligonucleotides indicate that UP1 binds specifically to (TTAGGG)$_3$ oligonucleotide. This result is entirely consistent with the demonstration that UP1 promotes telomere elongation and further supports the notion that UP1 activity is mediated through direct binding to single-stranded telomeric repeats. It remains to be shown whether UP1 associates with telomeric repeats in vivo.

Although the present invention has been described hereinabove by way of preferred embodiments thereof, it can be modified, without departing from the spirit and nature of the subject invention as defined in the appended claims.

What is claimed is:

1. A method of modulating the length of telomeres, comprising the step of administering to a cell in vitro, an amount of a molecule sufficient to modulate telomere length, wherein said molecule is:
   a) a nucleic acid sequence encoding hnRNP A1;
   b) a nucleic acid sequence encoding UP1;
   c) a trypsin-like protease involved in the conversion of hnRNP A1 into UP1;
   d) a purified hnRNP A1 polypeptide;
   e) a purified UP1 polypeptide;
   f) an hnRNP A1 nucleic acid molecule that is in vitro mutagenized in the portion which is absent in UP1, or a deletion, insertion, or fusion of the nucleic acid molecule of a) or b);
   g) an hnRNP A1 polypeptide that is in vitro mutagenized in the portion which is absent in UP1, or a deletion, insertion, or fusion of the molecule of any of c)-e); or
   h) an agent which is specific for hnRNP A1 and/or UP1.

2. The method of claim 1, wherein the modulation comprises the increase or stabilization of the length of telomeres.

3. The method of claim 1, wherein the modulation comprises the decrease or destabilization of the length of telomeres.

4. The method of claim 3, wherein said agent is selected from the group comprising an antibody having specific binding affinity to a polypeptide or epitope bearing portion of hnRNP A1 or UP1.

5. The method of claim 3, wherein said agent is selected from the group comprising an antisense complementary to a nucleic acid encoding hnRNP A1 or a ribozyme that cleaves hnRNP A1.

6. The method of claim 5, wherein said ribozyme is a tetrahymena-type ribozyme.

7. The method of claim 5, wherein said ribozyme is a hammerhead-type ribozyme.

8. The method of claim 4, wherein the antibody is a monoclonal antibody.

9. A method for extending the ability of a cell to replicate, comprising the step of introducing in said cell in vitro an amount, sufficient to extend replication of said cell, of at least one of the following molecules:
   a) a nucleic acid sequence encoding hnRNP A1 or UP1;
   b) a purified hnRNP A1 polypeptide, or a purified UP1 polypeptide;
   c) a trypsin-like protease involved in the conversion of hnRNP A1 into UP1,
   d) an hnRNP A1 nucleic acid molecule that is in vitro mutagenized in the portion which is absent in UP1, or a deletion, insertion, or fusion of the nucleic acid molecule of a); or
   e) an hnRNP A1 polypeptide that is in vitro mutagenized in the portion which is absent in UP1, or a deletion, insertion, or fusion of the molecule of b) or c).

10. The method of claim 9, wherein said cell is a primary cell, and wherein said introduction thereinto of a nucleic acid sequence encoding hnRNP A1 or UP1, immortalizes said primary cell.

11. The method according to claim 10, wherein said nucleic acid sequence is present on a recombinant plasmid.

12. The method according to claim 10, wherein said recombinant plasmid is an expression vector.

13. The method of claim 9, wherein said cell is a compromised cell from a patient affected by Alzheimer's or Parkinson's diseases.

14. A telomere length modulating composition comprising at least one molecule selected from the group consisting of a nucleic acid sequence encoding UP1, a trypsin-like protease involved in the conversion of hnRNP A1 into UP1, a purified hnRNP A1 polypeptide, a purified UP1 polypeptide, a deletion, insertion, or fusion of a nucleic acid molecule encoding UP1; a deletion, insertion, or fusion of a trypsin-like protease involved in the conversion of hnRNP A1 into UP1; and a deletion, insertion, or fusion of an hnRNP A1 or UP1 polypeptide, together with a suitable carrier.

15. The telomere length modulating composition of claim 14, comprising an effective amount of hnRNP A1 polypeptide or UP1 polypeptide, and wherein said composition increases or stabilizes said telomere length.

16. A telomere length modulating composition comprising an agent specific for hnRNP A1 or UP1, which interferes with the activity of hnRNP A1 or UP1 in increasing the length of telomeres, and wherein said composition destabilizes or decreases said telomere length, together with a suitable carrier.

17. The method of claim 1, wherein said molecule is an hnRNP A1 nucleic acid molecule that is in vitro mutagenized in the portion which is absent in UP1, or a deletion, insertion, or fusion of the nucleic acid molecule of a) or b).

18. The method of claim 1, wherein said molecule is an hnRNP A1 polypeptide that is in vitro mutagenized in the portion which is absent in UP1, or a deletion, insertion, or fusion of the molecule of any of c)-e).

19. The method of claim 9, wherein said molecule is an hnRNP A1 nucleic acid molecule that is in vitro mutagenized in the portion which is absent in UP1, or a deletion, insertion, or fusion of the nucleic acid molecule of a).

20. The method of claim 9, wherein said molecule is an hnRNP A1 polypeptide that is in vitro mutagenized in the portion which is absent in UP1, or a deletion, insertion, or fusion of the molecule of b) or c).

21. The method of claim 1, wherein said agent further interferes with the activity of hnRNP A1 in modulating the length of telomeres.

* * * * *

UNITED STATES PATENT AND TRADEMARK OFFICE
CERTIFICATE OF CORRECTION

PATENT NO.     : 6,294,332 B1
DATED          : September 25, 2001
INVENTOR(S)    : Benoit Chabot It is certified that error appears in the above-identified patent and that said Letters Patent is hereby corrected as shown below:

Title page,
Item [56], U.S. PATENT DOCUMENTS, replace "5,837,857 11/1998" with
-- 5,837,857 2/1996 --;
OTHER PUBLICATIONS, "Riva et al.," reference, replace "Embo" with -- EMBO --;
"Conrad et al.," reference, replace "Chromosomes" with -- Chromosome --;
"Burd et al.," reference, replace "Embo" with -- EMBO --;
"Mayeda et al.," reference, replace "Embo" with -- EMBO --;
"De Lange Titia," reference, replace "De Lange Titia" with -- De Lange, Titia --;
"De Lange, Titia," reference, replace "Dynamic" with -- Dynamics --;
"Zakian, Virginia A.," reference, replace "Begining" with -- Beginning --;
"Virta-Pearlman et al.," reference, replace "has properties" with -- has the properties --.

Column 1,
Line 24, replace "double strander" with -- double-stranded --;
Line 25, replace "single-stranded repeats" with -- single-stranded G-rich repeats --;
Line 35, replace "9:732" with -- 29:732 --;
Line 35, replace "630:751" with -- 63:751 --;
Line 37, replace "§67:815" with -- 67:815 --;
Line 41, replace "Inst" with -- Inst. --;
Line 47, replace "Maintenar" with -- maintenance of --;
Line 47, replace "teloees" with -- telomeres --;
Line 48, replace "suival" with -- survival --;
Line 48, replace "The Collectirg" with -- The Collecting --;
Line 52, replace "Genet" with -- Genet. --;
Line 60, replace "25.585" with -- 25:585 --;
Line 67, replace "ofthe" with -- of the --;

Column 2,
Line 10, replace "Human cells cultures" with -- Human cells cultured --;
Line 13, replace "Emp." with -- Exp. --;
Line 16, replace "telomec" with -- telomeric --;
Line 18, replace "Genet" with -- Genet. --;
Line 46, replace "elation" with -- elongation --;
Line 54, replace "antsense" with -- antisense --;
Line 54, replace "telomere RNA" with -- telomerase RNA --;
Line 55, replace "The author" with -- The Authors --;

UNITED STATES PATENT AND TRADEMARK OFFICE
CERTIFICATE OF CORRECTION

PATENT NO. : 6,294,332 B1
DATED : September 25, 2001
INVENTOR(S) : Benoit Chabot It is certified that error appears in the above-identified patent and that said Letters Patent is hereby corrected as shown below:

Column 3,
Line 17, replace "measuemert" with -- measurement --;
Line 21, replace "proteins mammalian" with -- proteins in mammalian --;
Line 50, replace "th direct" with -- the direct --;
Line 52, replace "expement" with -- experiment --;
Line 55, replace "(UPl)" with -- A1 (UP1) --;

Column 4,
Line 12, replace "vitro" with -- vivo --;
Line 14, replace "expessing" with -- expressing --;
Line 19, replace "a of" with -- α of --;
Line 29, replace "exress" with -- express --;
Line 39, replace "Sang et al." with -- Sarig et al. --;
Line 59, replace "chomosomal" with -- chromosomal --;

Column 5,
Line 6, replace "hnRP" with -- hnRNP --;
Line 9, replace "In additian this" with -- In addition, this --;
Line 24, replace "data ta" with -- data that --;
Line 35, replace "inceased;" with -- increased; --;
Line 41, replace "atherosclerosis)" with -- atherosclerosis). --;
Line 55, replace "infection. with" with -- infection with --;
Line 65, replace "contraindication" with -- contra-indication --;

Column 6,
Line 9, replace "e., telornere" with -- e.g., telomere --;
Line 11, replace "thrapeutically" with -- therapeutically --;
Line 36, replace "theabsence" with -- the absence --;
Line 37, replace "ouTin" with -- occurring --;
Line 38, replace "telofere" with -- telomere --;
Line 38, replace "e o cell" with -- expanding cell --;
Line 42, replace "modulting" with -- modulating --;
Line 42, replace "lengh" with -- length --;
Line 50, replace "skill" with -- skill. --;

UNITED STATES PATENT AND TRADEMARK OFFICE
CERTIFICATE OF CORRECTION

PATENT NO.     : 6,294,332 B1
DATED          : September 25, 2001
INVENTOR(S)    : Benoit Chabot It is certified that error appears in the above-identified patent and that said Letters Patent is hereby corrected as shown below:

Column 7,
Line 35, replace "patient" with -- patient. --;
Line 64, replace "typsin-like" with -- trypsin-like --;
Line 66, replace "withe" with -- with the --;

Column 8,
Line 22, replace "trypsin-ike" with -- trypsin-like --;
Line 25, replace "Therapeutically" with -- therapeutically --;
Line 35, replace "evident" with -- evident. --;
Line 39, replace "undertood" with -- understood that --;
Line 66, replace "approahes" with -- approaches --;

Column 9,
Line 4, replace "death" with -- death. --;
Line 7, replace "immortal" with -- immortal. --;
Line 20, replace "plasmacytomna" with -- plasmacytoma --;
Line 28, replace "target" with -- target. --;
Line 31, replace "are" with -- antisense --;
Line 32, replace "an" with -- ordinary --;
Line 34, replace "to" with -- the --;
Line 65, replace "enclude" with -- include --;

Column 10,
Line 1, replace "telomer" with -- telomeres --;
Line 3, replace "Me" with -- the --;
Line 25, replace "therpeuroc" with -- therapeutic --;
Line 56, replace "te" with -- the --;
Line 63, replace "Set" with -- affects --;
Line 64, replace "length" with -- length. --;

Column 11,
Line 1, replace "monocional" with -- monoclonal --;
Line 5, replace "erythroleukaemic" with -- erythroleukemic --;
Line 10, replace "Sc." with -- Sci. --;
Line 19, replace "GP+-A86" with -- GP+A-86 --;
Line 26, replace "CB3-Ala" with -- CB3-A1α --;

UNITED STATES PATENT AND TRADEMARK OFFICE
CERTIFICATE OF CORRECTION

PATENT NO. : 6,294,332 B1
DATED : September 25, 2001
INVENTOR(S) : Benoit Chabot It is certified that error appears in the above-identified patent and that said Letters Patent is hereby corrected as shown below:

Column 11 cont'd,
Line 30, replace "extract" with -- extracts --;
Line 32, replace "right" with -- right. --;
Line 37, replace "unlabelied" with -- unlabelled --;
Line 46, replace "(TCCCTAA)$_3$" with -- (CCCTAA)$_3$ --;
Line 47, replace "CB83" with -- CB3 --;
Line 51, replace "Mat" with -- that --;
Line 56, replace "right" with -- right. --;
Line 59, replace "as te" with -- as the --;
Line 62, replace "squns" with -- sequences --;
Line 64, replace "both th" with -- both the --;
Line 64, replace "UP1 contain sepuences" with -- UPl constructs contain sequences --;

Column 12,
Line 23, replace "mocknfected and viusinfected" with -- mock-infected and virus-infected --;
Line 26, replace "$10^4$. cells" with -- $10^4$ cells --;
Line 30, replace "extrad" with -- extract --;
Line 46, replace "oligonudeotides" with -- oligonucleotides --;
Line 52, replace "lies" with -- lines --;
Line 54, replace "Leukaemia" with -- Leukemia --;
Line 58, replace "Molec" with -- Molec. --;
Line 60, replace "nonmal" with -- normal --;

Column 13,
Line 1, replace "ENMBO" with -- EMBO --;
Line 9, replace "1B." with -- 1B, --;
Line 10, replace "te TRFs" with -- the TRFs --;
Line 11, replace "1B." with -- 1B, --;
Line 16, replace "CDNA" with -- cDNA --;
Line 17, replace "pomolor" with -- promotor --;
Line 26, replace "Mat" with -- that --;
Line 26, replace "was to" with -- was restored to --;
Line 28, replace "G418resistant" with -- G418-resistant --;
Line 30, replace "infection" with -- Infection --;
Line 43, replace "FIg." with -- Fig. --;

UNITED STATES PATENT AND TRADEMARK OFFICE
CERTIFICATE OF CORRECTION

PATENT NO. : 6,294,332 B1
DATED : September 25, 2001
INVENTOR(S) : Benoit Chabot It is certified that error appears in the above-identified patent and that said Letters Patent is hereby corrected as shown below:

Column 13 cont'd,
Line 49, replace "CB3A1" with -- CB3-A1 --;
Line 50, replace "infection" with -- Infection --;
Line 56, replace "et Fat" with -- indicate that --;
Line 58, replace "(data not" with -- (data not shown). --;
Line 61, replace "Cáeres" with -- Cáceres --;

Column 14,
Line 10, replace "A1   M" with -- A1-M --;
Line 14, replace "A1-1647" with -- A1-647 --;
Line 16, replace "sequene" with -- sequence --;
Line 20, replace "UP1 was subcioned" with -- UP1 fragment was subcloned --;
Line 52, replace "d(CCCTMA)$_3$" with -- d(CCCTAA)$_3$ --;
Line 55, replace "(Fig. 3,2-8)." with -- (Fig. 3, lanes 2-8). --;

Column 15,
Line 1, replace "telomerase-medication" with -- telomerase-mediated --;
Line 14, replace "NaU." with -- Nat. --;
Line 20, replace "telomers" with -- telomere --;
Lines 46-47, replace "oFe fi dA1in" with -- that modulates the function of A1 in --;
Line 47, replace "biogenesis" with -- biogenesis. --;
Line 48, replace "single-band" with -- single-stranded --;
Line 51, replace "nudeolytic" with -- nucleolytic --;
Line 52, replace "polymerase a" with -- polymerase α --;
Line 53, replace "single-st" with -- single-stranded --;
Line 58, replace "immoralization" with -- immortalization --;

Column 16,
Line 17, replace "Primary, Cells" with -- Primary Cells --;
Line 62, replace "G4l 8" with -- G418 --;
Line 63, replace "1 ml" with -- 100 ml --;

Column 17,
Line 9, replace "Removnng" with -- Removing --;
Line 9, replace "supernant" with -- supernatant --;
Line 9, replace "gron" with -- grown --;
Lines 20-21, replace "containin" with -- containing --;

UNITED STATES PATENT AND TRADEMARK OFFICE
CERTIFICATE OF CORRECTION

PATENT NO. : 6,294,332 B1
DATED : September 25, 2001
INVENTOR(S) : Benoit Chabot It is certified that error appears in the above-identified patent and that said Letters Patent is hereby corrected as shown below:

Column 17 cont'd,
Line 23, replace "It was have already" with -- It was already --;
Line 23, replace "variety mouse" with -- variety of mouse --;
Line 23, replace "incduding" with -- including --;
Line 23, replace "erythroleukaemic" with -- erythroleukemic --;
Line 24, replace "CB3." with -- CB3, --;
Line 36, begin a new line and indent after "1) Extraction of DNA";
Line 36, replace "resuspened" with -- resuspended --;
Line 37, replace "epperndof" with -- eppendorf --;
Line 40, replace "containig" with -- containing --;
Line 44, replace "Mte aqeous" with -- the aqueous --;
Line 46, replace "DNA" with -- DNA. --;
Line 65, replace "(ex" with -- (ex: --;
Line 67, replace "the is" with -- the --;
Line 67, replace "glycol" with -- glycerol --;

Column 18,
Line 3, replace "NA$_2$EDTA," with -- Na$_2$EDTA, --;
Line 4, replace "Ih." with -- 1h. --;
Line 5, replace "thiess" with -- thickness --;
Line 6, replace "to" with -- the --;
Line 28, replace "3 µof" with -- 3µl of --;
Line 39, replace "1) Cell LYSIS" with -- 1) Cell Lysis --;
Line 41, replace "NA$_2$HPO$_4$" with -- Na$_2$HPO$_4$ --;
Line 43, replace "500 µPBS-A" with -- 500 µl PBS-A --;
Line 47, replace "for a" with -- for --;
Line 48, replace "polyacrylame/SDS" with -- polyacrylamide/SDS --;
Line 51, replace "Tss-Baseo" with -- Tris-Base --;
Line 58, replace "milk/SD" with -- milk/SDS --;
Line 60, replace "Tri-base" with -- Tris-base --;

Column 19,
Line 24, replace "leukaemia" with -- leukemia --;
Line 56, replace "atisense" with -- antisense --;
Line 57, replace "Fe" with -- the --;
Line 63, replace "telemeres" with -- telomeres --;

UNITED STATES PATENT AND TRADEMARK OFFICE
CERTIFICATE OF CORRECTION

PATENT NO.   : 6,294,332 B1
DATED        : September 25, 2001
INVENTOR(S)  : Benoit Chabot It is certified that error appears in the above-identified patent and that said Letters Patent is hereby corrected as shown below:

Column 20,
Line 16, replace "ExDression" with -- Expression --;
Line 46, replace "intedere" with -- interfere --;
Line 49, replace "aftering" with -- altering --;
Line 51, replace "exprssion" with -- expression --;
Line 52, replace "te" with -- the --;
Line 56, replace "mammnary" with -- mammary --;

Column 21,
Line 11, replace "disply" with -- display --;
Line 15, replace "teloreres" with -- telomeres --;

Column 22,
Line 7, replace "TTAGGG)$_3$" with -- (TTAGGG)$_3$ --.

Signed and Sealed this

Twenty-sixth Day of August, 2003

JAMES E. ROGAN
*Director of the United States Patent and Trademark Office*

SEQUENCE LISTING

```
<160> NUMBER OF SEQ ID NOS:  10

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
ccctaaccct aaccctaa                                                        18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
ttagggttag ggttaggg                                                        18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gggtgtgggt gtgtgtggtg gg                                                   22

<210> SEQ ID NO 4
<211> LENGTH: 25
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
aattcttttg ctcgacgctg ccgag                                            25

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
aattctgtca gcgacctctc tgactggatg a                                     31

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ccaggatagg gtcactag                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ggttagggtt agggttag                                                    18

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ggttagggtt agggttaggg ttag                                             24

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttggggttgg ggttgggg                                                    18

<210> SEQ ID NO 10
<211> LENGTH: 24
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 10
tttgggtttg ggtttgggtt tggg                                              24
```